United States Patent [19]

Kamata et al.

[11] 4,394,505
[45] Jul. 19, 1983

[54] 5-FLUOROURACIL DERIVATIVES

[75] Inventors: Susumu Kamata, Takarazuka; Wataru Nagata, Nishinomiya, both of Japan

[73] Assignee: Shionogi & Co., Ltd., Osaka, Japan

[21] Appl. No.: 369,110

[22] Filed: Apr. 16, 1982

[30] Foreign Application Priority Data

Apr. 28, 1981 [JP] Japan ................................ 56-64738

[51] Int. Cl.³ ................ C07D 487/04; C07D 498/04; C07D 513/04
[52] U.S. Cl. ............................. 544/91; 260/243.3; 424/246; 424/248.57; 424/248.58; 424/251; 544/48; 544/69; 544/229; 544/278; 544/279; 544/281
[58] Field of Search ............... 260/243.3; 544/48, 69, 544/91, 229, 278, 279, 281

[56] References Cited

U.S. PATENT DOCUMENTS 3,704,304  11/1972  Wei et al. ........................... 544/278
3,888,983  6/1975  Baetz ............................... 544/278 X
4,024,143  5/1977  Schuman et al. ................... 544/229
4,329,460  5/1982  Miyashita et al. ................. 544/299 X Primary Examiner—Richard Raymond
Attorney, Agent, or Firm—Wenderoth, Lind & Ponack

[57] ABSTRACT

Novel 5-fluorouracil derivatives of the following general formula

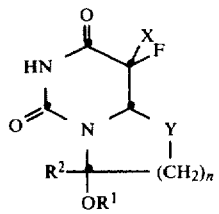

wherein
  $R^1$ is hydrogen, $C_1$-$C_5$alkyl, $C_6$-$C_{10}$aryl, $C_7$-$C_{10}$aralkyl, $C_1$-$C_{12}$alkanoyl, $C_2$-$C_6$alkoxycarbonyl, $C_1$-$C_5$alkanoyloxymethyl, carbamoyl or tri-$C_1$-$C_5$alkylsilyl;
  $R^2$ is hydrogen, $C_1$-$C_5$alkyl, $C_6$-$C_{10}$aryl or $C_7$-$C_{10}$aralkyl;
  X is hydrogen, halogen or $C_2$-$C_6$alkoxycarbonyl;
  Y is O, NR' (R' is hydrogen or $C_1$-$C_5$alkyl), S, SO or $SO_2$; and
  n is an integer of 1–3.

which are orally administrable anti-tumor agents.

5 Claims, No Drawings

5-FLUOROURACIL DERIVATIVES

BACKGROUND OF THE INVENTION

1. Field of the Invention

The invention relates to novel 5-fluorouracil derivatives, which are orally applicable anti-tumor agents.

2. Description of the Prior Art

5-Fluorouracil (hereinafter abbreviated as 5 FU) has widely been used in treatment of malignant tumors as antimetabolic anti-tumor agents. The anti-tumor activity of 5 FU is very strong, but it has many disadvantages such as the restricted scope of application, limited dosage, forbidden continuous administration over long periods and difficult oral application because of its strong toxicity and adverse reaction of frequent occurrence. As a modified 5 FU derivative, FT-207 [1-(2-tetrahydrofuryl)5-fluorouracil] [Ftorafur ® (Taiho Yakuhin); Jap. Pat. Unexam. Pub. Nos. 50-50383; 50-50384; 50-64281; 51-14682; 53-84981] which is a less toxic, orally and continuously administrable derivative, the activity of which is, however, insufficient, is now commercially available. Other 5 FU derivatives under clinical evaluation, for example, HCFU [1-n-hexylcarbamoyl-5-fluorouracil] [Mitsui Seiyaku; Jap. Pat. Unexam. Pub. No. 50-148365] are known.

SUMMARY OF THE INVENTION

The present invention relates to novel 5-fluorouracil derivatives. More particularly, it relates to orally applicable novel anti-tumor compounds, 5-fluorouracil derivatives, which are represented by the following general formula (I).

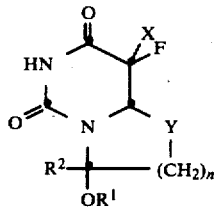

wherein
R[1] is hydrogen, $C_1$-$C_5$alkyl, $C_6$-$C_{10}$aryl, $C_7$-$C_{10}$aralkyl, $C_1$-$C_{12}$alkanoyl, $C_2$-$C_6$alkoxycarbonyl, $C_1$-$C_5$alkanoyloxymethyl, carbamoyl or tri-$C_1$-$C_5$alkylsilyl;
R[2] is hydrogen, $C_1$-$C_5$alkyl, $C_6$-$C_{10}$aryl or $C_7$-$C_{10}$aralkyl;
X is hydrogen, halogen or $C_2$-$C_6$alkoxycarbonyl;
Y is O, NR' (R' is hydrogen or $C_1$-$C_5$alkyl), S, SO or $SO_2$; and
n is an integer of 1-3.

DESCRIPTION OF THE PREFERRED EMBODIMENTS

The purpose of the present invention is to provide 5 FU derivatives of pro-drug type in order to make varied application forms possible, particularly to provide orally administrable derivatives with less adverse reaction, and to improve permeability of 5 FU to the tumor cells. The present invention offers the compounds of the above general formula (I) as 5 FU derivatives which are suitable for these purposes.

The objective compounds in the present invention are represented by the general formula (I):

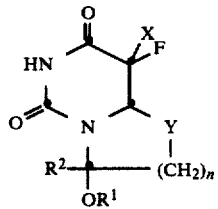

wherein
R[1] is hydrogen, $C_1$-$C_5$alkyl, $C_6$-$C_{10}$aryl, $C_7$-$C_{10}$aralkyl, $C_1$-$C_{12}$alkanoyl, $C_2$-$C_6$alkoxycarbonyl, $C_1$-$C_5$alkanoyloxymethyl, carbamoyl or tri-$C_1$-$C_5$alkylsilyl;
R[2] is hydrogen, $C_1$-$C_5$alkyl, $C_6$-$C_{10}$aryl or $C_7$-$C_{10}$aralkyl;
X is hydrogen, halogen or $C_2$-$C_6$ alkoxycarbonyl;
Y is O, NR' (R' is hydrogen or $C_1$-$C_5$alkyl), S, SO or $SO_2$; and
n is an integer of 1-3.

In the definition of the above general formula (I), $C_1$-$C_5$alkyl means a straight or branched chain lower alkyl of 1-5 carbon atoms, e.g., methyl, ethyl, propyl, isopropyl, butyl, isobutyl, sec-butyl, and pentyl. $C_6$-$C_{10}$Aryl means phenyl or naphthyl of 6-10 carbon atoms which may be substituted by lower alkyls (e.g. methyl, ethyl, propyl), lower alkoxys (e.g., methoxy, ethoxy, propoxy), halogen (e.g., fluoro, chloro, bromo), nitro and the like, including phenyl, p-toluyl, p-methoxyphenyl, 2,4-dimethoxyphenyl, p-chlorophenyl and p-nitrophenyl. $C_7$-$C_{10}$Aralkyl means benzyl or phenethyl of 7-10 carbon atoms which may be substituted, including benzyl, p-methoxybenzyl, p-chlorobenzyl, p-toluyl, phenethyl and (3,5-dimethylphenyl)ethyl. $C_1$-$C_{12}$Alkanoyl means an alkanoic acid residue of 1-12 carbon atoms derived from fatty acids, e.g., formyl, acetyl, propionyl, butyryl, valeryl, pivaloyl, and octanoyl, $C_2$-$C_6$Alkoxycarbonyl means a straight or branched chain lower alkoxycarbonyl of 2-6 carbon atoms, e.g., methoxycarbonyl, ethoxycarbonyl, propoxycarbonyl, isopropoxycarbonyl, t-butoxycarbonyl, and pentoxycarbonyl. $C_1$-$C_5$Alkanoyloxymethyl means an oxymethyl substituted by an alkanoyl of 1-5 carbon atoms, e.g., acetyloxymethyl, propionyloxymethyl, butyryloxymethyl, and pivaloyloxymethyl. Tri- $C_1$-$C_5$alkylsilyl means a group in which the silyl is substituted by 3 $C_1$-$C_5$alkyls mentioned above, e.g., trimethylsilyl, triethylsilyl, tripropylsilyl, tripentylsilyl, and t-butyldimethylsilyl. Halogen includes chloro, bromo and iodo.

Representative of the objective compounds in the present invention are:

8α-Bromo-8β-fluoro-3α-hydroxy-2,3,6,7,8,8aα-hexahydro-5,7-dioxo-5H-oxazolo[3,2-c]pyrimidine, 8β-Fluoro-3α-hydroxy-2,3,6,7,8,8aα-hexahydro-5,7-dioxo-5H-oxazolo[3,2-c]pyrimidine, 3α-Acetoxy-8β-fluoro-2,3,6,7,8,8aα-hexahydro-5,7-dioxo-5H-oxazolo[3,2-c]pyrimidine, 8β-Fluoro-2,3,6,7,8,8aα-hexahydro-3α-octanoyloxy-5,7-dioxo-5H-oxazolo[3,2-c]pyrimidine, 8β-Fluoro-2,3,6,7,8aα-hexahydro-5,7-dioxo-3β-trimethylacetoxy-5H-oxazolo[3,2-c]pyrimidine, 3α-Acetoxy-8α-bromo-8β-fluoro-2,3,6,7,8,8aα-hexahydro-5,7-dioxo-5H-oxazolo[3,2-c]pyrimidine, 8α-Bromo-8β-fluoro-2,3,6,7,8,8aα-hexahydro-3α-octanoyloxy-5,7-dioxo-5H-oxazolo[3,2-c]pyrimidine, 8α-Bromo-8β-fluoro-2,3,6,7,8,8aα-hexahydro-5,7-dioxo-3α-trimethylacetoxy-5H-oxazolo[3,2-c]pyrimidine,
3α-(tert-Butyldimethylsilyloxy)-8α-bromo-8β-fluoro-2,3,6,7,8,8aα-hexahydro-5,7-dioxo-5H-oxazolo[3,2-c]pyrimidine,
3α-(tert-Butyldimethylsilyloxy)-8α-fluoro-2,3,6,7,8,8aα-hexahydro-5,7-dioxo-5H-oxazolo[3,2-c]pyrimidine,
3α-(tert-Butyldimethylsilyloxy)-8β-fluoro-2,3,6,7,8,8aα-hexahydro-5,7-dioxo-5H-oxazolo[3,2-c]pyrimidine,
8α-Fluoro-3α-hydroxy-2,3,6,7,8,8aα-hexahydro-5,7-dioxo-5H-oxazolo[3,2-c]pyrimidine,
3α-Acetoxy-8α-fluoro-2,3,6,7,8,8aα-hexahydro-5,7-dioxo-5H-oxazolo[3,2-c]pyrimidine,
8α-Fluoro-2,3,6,7,8,8aα-hexahydro-3α-octanoyloxy-5,7-dioxo-5H-oxazolo[3,2-c]pyrimidine,
8α-Fluoro-2,3,6,7,8,8aα-hexahydro-5,7-dioxo-3α-trimethylacetoxy-5H-oxazolo[3,2-c]pyrimidine,
9α-Bromo-9β-fluoro-3,4,7,8,9,9aα-hexahydro-4α-hydroxy-6,8-dioxo-2H,6H-[1,3]-oxazino[3,2-c]pyrimidine,
9β-Fluoro-6,8-dioxo-4α-hydroxy-3,4,7,8,9,9aα-hexahydro-2H,6H-[1,3]-oxazino[3,2-c]pyrimidine,
4α-(tert-Butyldimethylsilyloxy)-7-tert-butyldimethylsilyl-9α-bromo-9β-fluoro-3,4,7,8,9,9aα-hexahydro-6,8-dioxo-2H,6H-[1,3]-oxazino[3,2-c]pyrimidine,
9α-Fluoro-3,4,7,8,9,9aα-hexahydro-4α-hydroxy-6,8-dioxo-2H,6H-[1,3]-oxazino[3,2-c]pyrimidine,
9α-Fluoro-3,4,7,8,9,9aα-hexahydro-4β-hydroxy-6,8-dioxo-2H,6H-[1,3]-oxazino[3,2-c]pyrimidine,
4α-Acetoxy-9α-bromo-9β-fluoro-3,4,7,8,9,9aα-hexahydro-6,8-dioxo-2H,6H-[1,3]-oxazino[3,2-c]pyrimidine,
4α-Acetoxy-9α-fluoro-3,4,7,8,9,9aα-hexahydro-6,8-dioxo-2H,6H-[1,3]-oxazino[3,2-c]pyrimidine,
4α-Acetoxy-9β-fluoro-3,4,7,8,9,9aα-hexahydro-6,8-dioxo-2H,6H-[1,3]-oxazino[3,2-c]pyrimidine,
9α-Bromo-9β-fluoro-3,4,7,8,9,9aα-hexahydro-4α-octanoyloxy-6,8-dioxo-2H,6H-[1,3]-oxazino[3,2-c]pyrimidine,
9α-Bromo-9β-fluoro-3,4,7,8,9,9aα-hexahydro-6,8-dioxo-4α-trimethylacetoxy-2H,6H-[1,3]-oxazino[3,2-c]pyrimidine,
9α-Fluoro-3,4,7,8,9,9aα-hexahydro-6,8-dioxo-4α-trimethylacetoxy-2H,6H-[1,3]-oxazino[3,2-c]pyrimidine,
9α-Fluoro-3,4,7,8,9,9aα-hexahydro-4α-octanoyloxy-6,8-dioxo-2H,6H-[1,3]-oxazino[3,2-c]pyrimidine,
9β-Fluoro-3,4,7,8,9,9aα-hexahydro-4α-octanoyloxy-6,8-dioxo-2H,6H-[1,3]-oxazino[3,2-c]pyrimidine.

The objective compounds (I) in the present invention can be produced from the known compounds according to the process shown in the following reaction sequence.

(1) X = halogen, Y = O

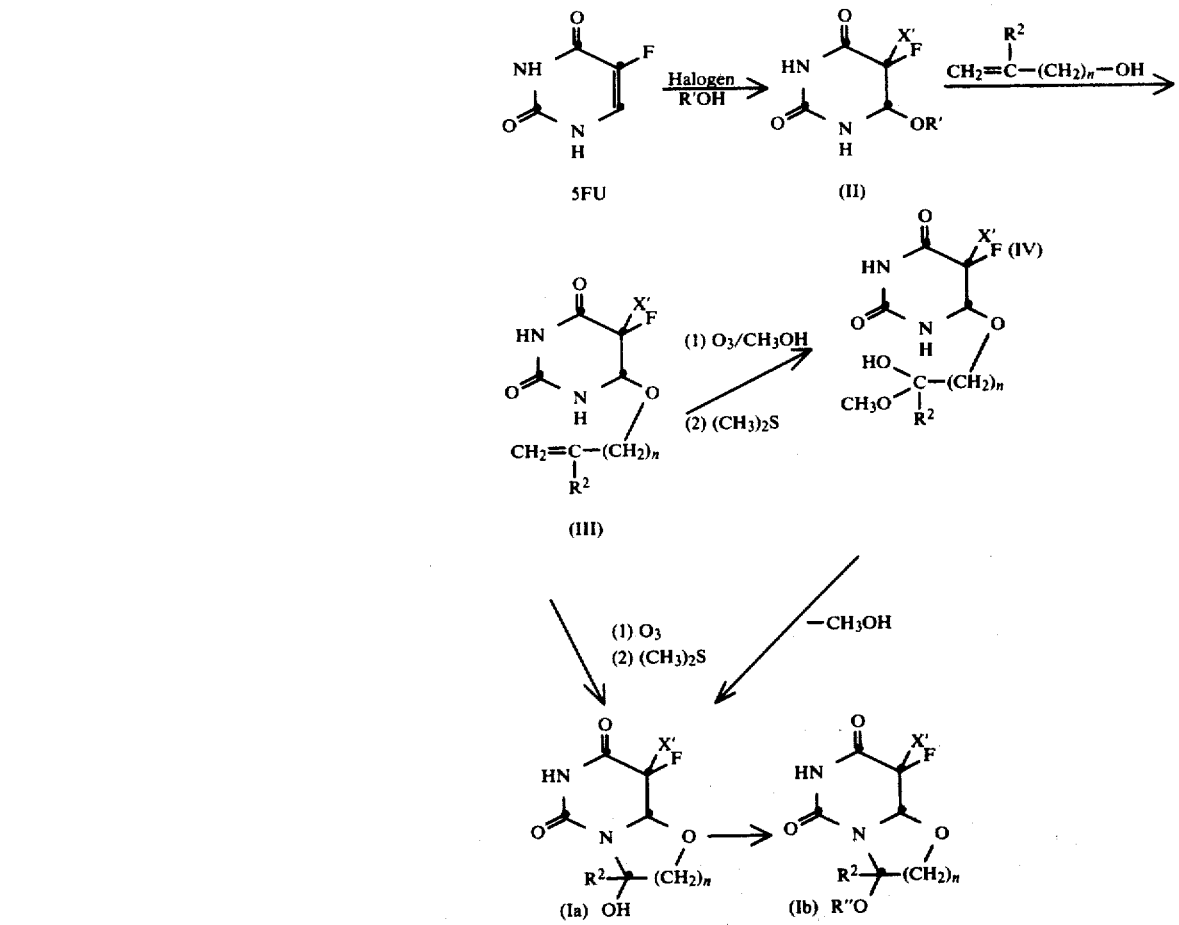

4α-(tert-Butyldimethylsilyloxy)-9α-fluoro-3,4,7,8,9,9aα-hexahydro-6,8-dioxo-2H,6H-[1,3]-oxazino-[3,2-c]pyrimidine,

[wherein R' is hydrogen, lower alkyl or lower alkanoyl; R" has the same significance as R¹ except for hydrogen;

X′ is halogen; $R^2$ and n have the same significance as mentioned above]

In the above reaction sequence, the conversion of the starting compound, 5 FU to the halogen adduct (II) is achieved by reacting 5 FU with lower alkanols or with lower alkanoic acids and the corresponding acid anhydride in the presence of a halogen such as $Br_2$, wherein the lower alkanols or alkanoic acids are represented by the general formula R′OH, according to the known methods, for example, described in J. Med. Chem. 10, 47 (1967).

The conversion of the halogen adducts (II) to the derivatives (III) is achieved on reaction with unsaturated alcohols represented by the general formula

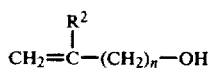

in the presence of a catalytic amount of acid, for example, methanesulfonic acid. The reaction may be conducted in or without a solvent under heating at the refluxing temperature for about 1–10 hours. As the reaction solvents, aprotic solvents such as benzene, toluene, acetone, acetonitrile, tetrahydrofuran, dioxane and N,N-dimethylformamide and the like may preferably be employed. In some instances the reaction may preferably be conducted in a reaction vessel equipped with a water separator containing Molecular sieves.

Ozonolysis of the alcohol adduct (III) gives the compounds (Ia), one of the objective compounds in the present invention. The reaction may be conducted under the conditions employed in the conventional ozonolysis. In addition to this process of producing the compounds (Ia) directly from the compounds (III) by ozonolysis, the compounds (Ia) may be prepared through the stable intermediates (IV) by ozonolysis followed by elimination of methanol accompanied by cyclization. The stable intermediate (IV) in ozonolysis can be obtained by carrying out the reaction in the presence of methanol.

The acylation or alkylation of the compound (Ia) according to the known method gives the compound (Ib) in which $R^1$ is not hydrogen.

The compounds in which Y is not O but NR′, S, SO and $SO_2$ can also be produced in the same way as in the compounds where Y is O.

(2) X = hydrogen, Y = 0

(a)

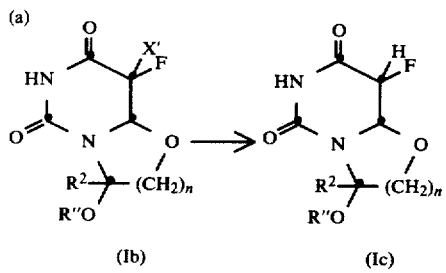

[wherein R″, X′ and n have the same significance as mentioned above]

In the general formula (I), the compounds in which $R^1$ is the same as in the above definition except for hydrogen, X is hydrogen and Y is O can be prepared from the compound (Ib) on reductive elimination of the halogen X′. As the reduction condition, hydrogenolysis with nickel, palladium, platinum or rhodium catalyst, or hydride reduction with tri-n-butyltin hydride can be employed. For example, in case of hydrogenolysis with a palladium catalyst, the reaction may be carried out under conditions where the catalytic hydrogenation is conducted in tetrahydrofuran, dioxane or a mixture of tetrahydrofuran-methanol in the presence of a weak base such as sodium acetate employing palladium-carbon as a catalyst. Alternatively, reduction with potassium hydrogensulfide (KSH) in an alcohol such as methanol and ethanol may also be employed.

(b)

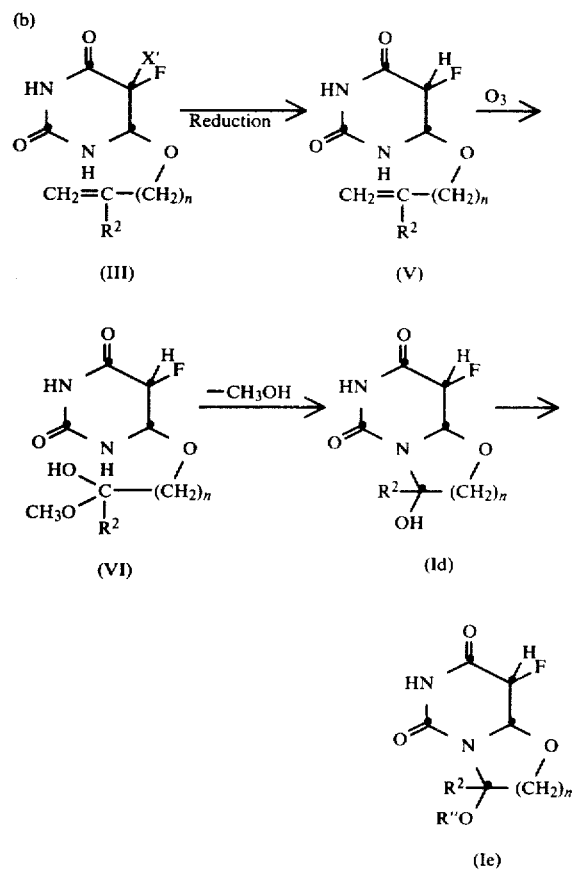

[wherein $R^2$, R″, X′ and n have the same significance as mentioned above]

The alcohol substituted derivatives (III) are reduced in the same manner as in the above step (a), and the subsequent reaction of the resulting compounds (V) may be carried out according to the reaction sequence via the above compounds (IV) to the compounds (Ia) and (Ib). The reaction in each step can be conducted in the same manner as mentioned above.

The reaction in the above steps (a) and (b) can also be applied in producing the compounds in which Y is not O but NR′, S, SO and $SO_2$ in the general formula (I).

(3) X = alkoxycarbonyl, Y = O

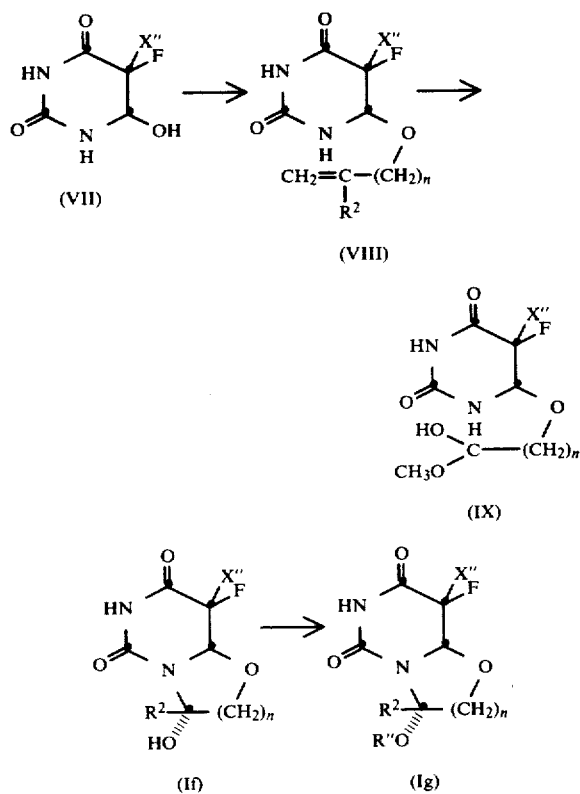

[wherein X" is $C_2$-$C_6$alkoxycarbonyl, and $R^2$, R" and n have the same significance as mentioned above]

The reaction of the starting compounds (VII) to the alcohol substituted compounds (VIII) can be carried out according to the substitution reaction of an unsaturated alcohol

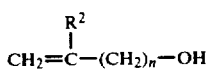

with the above compounds (II) to give (III). The reaction from the alcohol substituted compounds (VIII) to the compounds (IX), (If) and (Ig) can be achieved under the same conditions as in the reaction from the above compounds (III) to (Ia) and (Ib). The starting compounds (VII) and the intermediate (VIII) are known compounds, disclosed, for example, in Jap. Pat. Unexam. pub. No. 55-102573.

The compounds in which Y is not O but NR', S, SO and $SO_2$ in the general formula (I) can be produced in the same procedure as mentioned above.

Effect

The objective compounds (I) (Ia–g) in the present invention are orally applicable and have a superior anti-tumor action. For example, the anti-tumor activity of the compounds (I) against leukemia L1210 in mice is as follows.

(Test Method)

Ascites cells ($10^5$ cell) of leukemia L1210 in mice are diluted with physiological saline and intraperitoneally implanted in $BDF_1$ female mice of 5 weeks age. 8–10 Mice are employed in a control group, and 6–7 mice are employed in a test group to which the test compounds are given. A prefixed amount of the test compounds is administered to the mice of the test group intraperitoneally or orally successively for 5 days.

(Judgement of Effect)

From the average survival days in each test group and control group, the increase of lifespan (ILS) is calculated according to the following equation.

$$ILS(\%) = \frac{\left(\begin{array}{c}\text{Average survival}\\\text{days in administered}\\\text{group}\end{array}\right) - \left(\begin{array}{c}\text{Average survival}\\\text{days in control}\\\text{group}\end{array}\right)}{(\text{Average survival days in control group})} \times 100$$

From the dosage of maximum ILS value (maximum effective dose) and 30% ILS value (minimum effective dose), the chemotherapeutic index (CI) is calculated according to the following equation. The higher value indicates higher safety.

$$CI = \frac{\text{Maximum effective dose (mg/kg)}}{\text{Minimum effective dose (mg/kg)}}$$

(Compounds Tested)

A: 5FU

B: Ftorafur ®

C: dl-8α-Fluoro-2,3,6,7,8,8aα-hexahydro-5,7-dioxo-3α-trimethylacetoxy-5H-oxazolo[3,2-c]pyrimidine D: dl-8α-Fluoro-2,3,6,7,8,8aα-hexahydro-3α-octanoyloxy-5,7-dioxo-5H-oxazolo[3,2-c]pyrimidine E: dl-3α-Acetoxy-8α-fluoro-2,3,6,7,8,8aα-hexahydro-5,7-dioxo-5H-oxazolo[3,2-c]pyrimidine F: dl-9α-Fluoro-3,4,7,8,9,9aα-hexahydro-6,8-dioxo-4α-trimethylacetoxy-2H,6H-[1,3]-oxadino[3,2-c]pyrimidine (Result)

TABLE 1

| Dose | ILS value (%) of each compound administered intraperitoneally | | | |
|---|---|---|---|---|
| (mg × day) | A | B | C | E |
| 4 × 5 | 20 | — | — | — |
| 20 × 5 | 50 | — | — | — |
| 40 × 5 | 84 | 0 | 7 | 14 |
| 100 × 5 | 13 | 26 | 13 | 18 |
| 200 × 5 | — | 36 | 32 | 28 |
| 400 × 3 | — | 4 | 37 | 58 |
| 600 × 5 | — | — | 39 | — |

TABLE 2

| Compounds | CI value of each compound administered intraperitoneally | | | |
|---|---|---|---|---|
| | A | B | C | E |
| Maximum Effective Dose (mg/kg) | 200 | 1000 | — | 2000 |
| Minimum Effective Dose (mg/kg) | 40 | 700 | — | 1000 |
| CI Value | 5.0 | 1.4 | — | 2 |

TABLE 3

| Dose | ILS value (%) of each compound administered orally | | | | | |
|---|---|---|---|---|---|---|
| (mg × day) | A | B | C | D | E | F |
| 20 × 5 | 22 | — | — | — | — | — |
| 40 × 5 | 39 | 1 | — | 8 | 1 | 9 |
| 60 × 5 | 56 | — | — | — | — | — |
| 100 × 5 | 35 | 19 | 21 | 22 | −3 | 13 |
| 200 × 5 | — | 29 | 47 | 30 | 14 | 32 |
| 400 × 5 | — | 31 | 59 | 38 | 39 | 51 |

TABLE 3-continued

| ILS value (%) of each compound administered orally | | | | | | |
|---|---|---|---|---|---|---|
| Dose | Compounds Tested | | | | | |
| (mg × day) | A | B | C | D | E | F |
| 600 × 5 | — | −9 | 107 | 51 | 46 | 57 |

TABLE 4

| CI value of each compound administered orally | | | | | | |
|---|---|---|---|---|---|---|
| Compounds | A | B | C | D | E | F |
| Maximum Effective Dose (mg/kg) | 300 | 2000 | 3000 | 3000 | 2400 | 3000 |
| Minimum Effective Dose (mg/kg) | 150 | 1000 | 1000 | 1000 | 1200 | 1000 |
| CI Value | 2.0 | 2.0 | 3.0 | 3.0 | 2.0 | 3.0 |

Obviously as shown in the above result, the compounds (I) in the present invention have a superior anti-tumor action and can be applied to human or animals as anti-tumor agents.

In addition, the compounds (I) are advantageous in view of ease of increase or decrease of dosage, because the effective range of the dose is relatively wide.

The compounds (I) in the present invention can be administered to human or animals orally or parenterally. For example, the compounds (I) can be administered intravenously, intramuscularly, or subcutaneously, etc. as solutions or suspensions in a proper solvent for injection (e.g., distilled water for injection, ethanol, glycerol, propylene glycol, olive oil, peanut oil). In preparations for injection, the compounds (I) can be kept in ampoules in a form of solutions or suspensions, and more preferably preserved in ampoules or vials in a form of crystals, powder, fine crystals, lyophilizates, etc. and dissolved in water immediately before use. Stabilizer may be added. Moreover, the compounds (I) can be administered orally together with pharmaceutical components such as diluent (e.g., starch, sucrose, lactose, calcium carbonate, kaolin), lubricant (e.g., stearic acid, sodium benzoate, boric acid, silica, polyethylene glycol) in a form of powder, tablets, granules, capsules, troches and dry syrup.

The compounds (I) are generally administered orally at 500 mg-10 g dosage per adult 1-3 times a day in treatment of tumors. The dosage, however, may preferably be increased or decreased optionally according to the age, state, clinical history, etc. of the patient.

The following examples are provided to further illustrate this invention.

EXAMPLE 1

(A)

dl-5α-Bromo-5β-fluoro-1,2,3,4,5,6-hexahydro-2,4-dioxo-6β-(2-propenyloxy)pyrimidine (2)

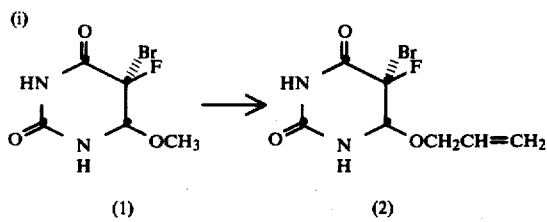

dl-5α-Bromo-5β-fluoro-1,2,3,4,5,6-hexahydro-6β-methoxy-2,4-dioxopyrimidine (1)* (89.1 g, 0.37 mol), 2-propen-1-ol (450 ml) and methanesulfonic acid (0.2 ml) are placed in a flask equipped with a Dien-Stark water separator charged with Molecular sieves 4A, and the mixture is stirred under reflux with heating for about 6 hours. The crystalline residue after removal of an excess amount of 2-propen-1-ol under reduced pressure is recrystallized from acetone-ether to give the title compound (2) (80.7 g). Yield: 81.7%, m.p. 196°-197° C.

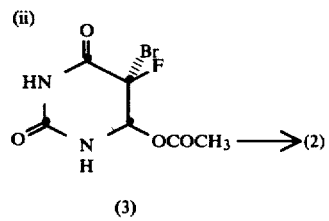

A mixture consisting of dl-6β-acetoxy-5α-bromo-5β-fluoro-1,2,3,4,5,6-hexahydro-2,4-dioxopyrimidine (3)* (2.69 g, 10 mmol), 2-propen-1-ol (30 ml) and methanesulfonic acid (0.1 ml) is stirred under reflux with heating for about 2 hours. After termination of the reaction, the mixture is cooled with ice, and sodium hydrogencarbonate (400 mg) is added thereto followed by stirring for 30 minutes. After removal of the insoluble material by filtration, an excess amount of 2-propen-1-ol is distilled off under reduced pressure to give crystalline residue, which is recrystallized from aceton-ether to give the title compound (2) (1.73 g). Yield: 65%. m.p. 196°-197° C.

(*)Note: dl-5α-Bromo-5β-fluoro-1,2,3,4,5,6-hexahydro-6β-methoxy-2,4-dioxopyrimidine and dl-6β-acetoxy-5α-bromo-5β-fluoro-1,2,3,4,5,6-hexahydro-2,4-dioxopyrimidine were produced according to the methods described in the following literature.
R. Duschinsky, T. Gabriel, W. Tautz, A. Nussbaum, M. Hoffer, E. Grunberg, J. H. Burchenal and J. J. Fox, J. Med. Chem., 10, 47 (1967)

(B)

dl-5α-Bromo-5β-fluoro-6β-(2-hydroxy-2-methoxyethoxy)-1,2,3,4,5,6-hexahydro-2,4-dioxopyrimidine (4)

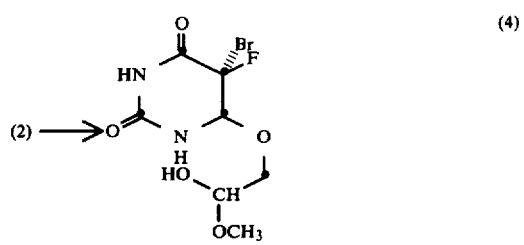

dl-5β-Fluoro-1,2,3,4,5,6-hexahydro-6β-(2-propenyloxy)-2,4-dioxopyrimidine (2) (10 g, 37 mmol) is dissolved in a mixture consisting of dichloromethane (200 ml) and methanol (100 ml), cooled to −78° C. in a dry ice-acetone bath, and then the mixture is ozonized by introducing ozone gas. After the reaction mixture turns blue, dimethylsulfide (13.7 ml) is added thereto, and the mixture is warmed up to 0° C. and allowed to react for about 1 hour. The crystalline residue after removal of the solvent by distillation is washed with dichloromethane to give the title compound (4) (9.7 g). Yield: 86.4%. m.p. 110°-116° C.

(C)
dl-8α-Bromo-8β-fluoro-3α-hydroxy-2,3,6,7,8,8aα-hexahydro-5,7-dioxo-5H-oxazolo[3,2-c]pyrimidine (5)

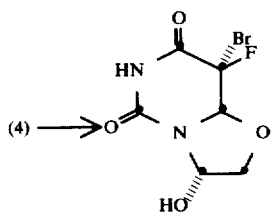

Molecular sieves 4A (100 g) is added to a solution of dl-5α-bromo-5β-fluoro-6β-(2-hydroxy-2-methoxyethoxy)-1,2,3,4,5,6-hexahydro-2,4-dioxopyrimidine (4) (24 g, 80 mmol) in tetrahydrofuran (530 ml), and the mixture is stirred at room temperature for 4 hours. Molecular sieves 4A is filtered off, and the solvent is distilled off. The resulting residue is crystallized from a mixture of benzene-ethyl acetate (2:1) to give the title compound (5) (16.1 g). Yield: 75.3%. m.p. 142°–143° C.

EXAMPLE 2

(A)
dl-5β-Fluoro-1,2,3,4,5,6-hexahydro-6β-(2-propenyloxy)-2,4-dioxopyrimidine (6)

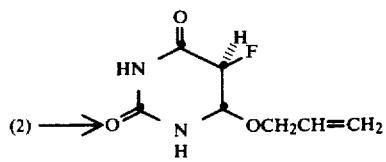

A solution of 86% potassium hydroxide (1.06 g, 22 mmol) dissolved in 2-propen-1-ol (25 ml) is cooled with ice, and hydrogen sulfide (about 700 mg, 20.6 mmol) is absorbed therein. dl-5α-Bromo-5β-fluoro-1,2,3,4,5,6-hexahydro-6β-(2-propenyloxy)-2,4-dioxopyrimidine (2) (4.33 g, 16.2 mmol) is slowly added thereto and allowed to stand at 0° C. for 10 minutes, at room temperature for 30 minutes, and at 65° C. for 20 minutes successively. The reaction mixture is cooled to room temperature, and the insoluble material is filtered off. Evaporation of the filtrate under reduced pressure gives crystalline residue, which is washed with iced water to give the title compound (6) (2.0 g). Yield: 66%. m.p. 171°–172° C.

(B)
dl-5β-Fluoro-6β-(2-hydroxy-2-methoxyethoxy)-1,2,3,4,5,6-hexahydro-2,4-dioxopyrimidine (7)

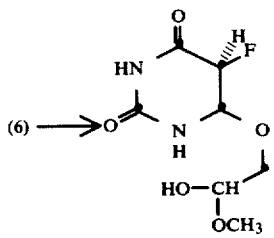

dl-5β-Fluoro-1,2,3,4,5,6-hexahydro-6β-(2-propenyloxy)-2,4-dioxopyrimidine (6) (3.85 g, 20.4 mmol) is dissolved in a mixture consisting of dichloromethane (150 ml) and methanol (150 ml), cooled to −78° C. in a dry ice-acetone bath, and then ozonized by introducing ozone gas. When the reaction mixture turns blue, supply of ozone is stopped, and an excess of ozone is exhausted by introducing nitrogen gas. Dimethylsulfide (40 ml) is added thereto, and the reaction mixture is warmed up to 0° C. and allowed to stand overnight. The resulting crystals are collected by filtration to give the title compound (7) (2.24 g). Yield: 49.2%. m.p. 176°–178° C. The mother liquor is evaporated, and the residue is purified by chromotography over silica gel employing a mixture of benzene-ethyl acetate (1:2) as eluent to give dl-8β-fluoro-3α-hydroxy-2,3,6,7,8,8aα-hexahydro-5,7-dioxo-5H-oxazolo[3,2-c]pyrimidine (8) (359 mg). Yield: 9.2%.

(C)
dl-8β-Fluoro-3α-hydroxy-2,3,6,7,8,8aα-hexahydro-5,7-dioxo-5H-oxazolo[3,2-c]pyrimidine (8)

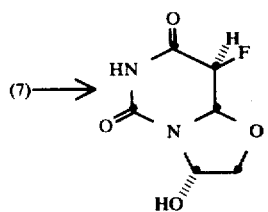

Molecular sieves 5A (about 2 g) is added to a solution of dl-5β-fluoro-6β-(2-hydroxy-2-methoxyethoxy)-1,2,3,4,5,6-hexahydro-2,4-dioxopyrimidine (7) (520 mg, 2.34 mmol) in tetrahydrofuran (30 ml) and stirred at room temperature for 3 hours. Removal of Molecular sieves 5A by filtration and evaporation of the solvent give crystalline residue, which is recrystallized from ethyl acetate-ether to give the title compound (8) (405 mg). Yield: 91%. m.p. 188°–191° C.

Alternatively, the title compound (8) is obtained in high yield from dl-5β-fluoro-6β-(2-hydroxy-2-methoxyethoxy)-1,2,3,4,5,6-hexahydro-2,4-dioxopyrimidine on elimination of methanol by chromatography over silica gel employing a mixture of benzene-ethyl acetate (1:2) as eluent, as mentioned in Example 2-B).

EXAMPLE 3 dl-3α-Acetoxy-8β-fluoro-2,3,6,7,8,8aα-hexahydro-5,7-dioxo-5H-oxazolo[3,2-c]pyrimidine (9):

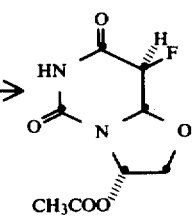

Acetic anhydride (3 ml) and pyridine (0.5 ml) are added to a solution of dl-8β-fluoro-3α-hydroxy-2,3,6,7,8,8aα-hexahydro-5,7-dioxo-5H-oxazolo[3,2-c]pyrimidine (8) (730 mg, 3.8 mmol) in tetrahydrofuran (5 ml), and the mixture is allowed to react at room temperature for 15 hours. The crystalline residue obtained after removal of an excess of reagents and the solvent is recrystallized from acetone-ether to give the title compound (9) (700 mg). Yield: 78.5%. m.p. 173°-174° C.

EXAMPLE 4 dl-8β-Fluoro-2,3,6,7,8,8aα-hexahydro-3α-octanoyloxy-5,7-dioxo-5H-oxazolo[3,2-c]pyrimidine (10):

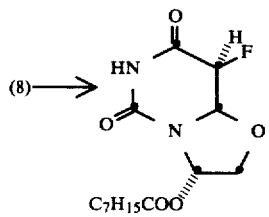

Octanoic anhydride (11.5 g, 43 mmol) and pyridine (3.48 ml) are added to a solution of dl-8β-fluoro-3α-hydroxy-2,3,6,7,8,8aα-hexahydro-5,7-dioxo-5H-oxazolo[3,2-c]pyrimidine (8) (2.36 g, 12.4 mmol) in tetrahydrofuran (50 ml), and the mixture is allowed to react at room temperature for 4 hours. After removal of an excess amount of reagents and the solvent, the product is purified by chromatography over silica gel employing a mixture of benzene-ethyl acetate (4:1) as eluent to give the title compound (10) (2.61 g). Yield: 67%. m.p. 58°-61° C.

EXAMPLE 5 dl-8β-Fluoro-2,3,6,7,8,8aα-hexahydro-5,7-dioxo-3α-trimethylacetoxy-5H-oxazolo[3,2-c]pyrimidine (11):

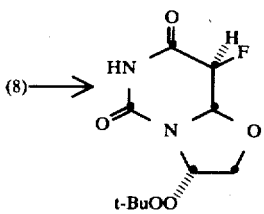

dl-8β-Fluoro-3α-hydroxy-2,3,6,7,8,8aα-hexahydro-5,7-dioxo-5H-oxazolo[3,2-c]pyrimidine (8) (1.9 g, 10 mmol) is dissolved in a mixture solution (70 ml) consisting of acetonitrile and tetrahydrofuran (1:1), and pivalic anhydride (16.2 ml, 80 mmol) is added, and then cooled to 0° C. After tin tetrachloride (1.17 ml, 10 mmol) is added at 0° C. in dropwise fashion, the reaction mixture is warmed up to room temperature and stirred for 2 hours. Anhydrous sodium hydrogencarbonate (4.2 g, 50 mmol) and a small amount of water are added thereto, and the mixture is allowed to react at room temperature for 30 minutes. The insoluble material is filtered off, and the solvent is distilled off. The product is purified by chromatography on a silica gel column employing a mixture of benzene-ethyl acetate (4:1) as eluent to give the title compound (11) (270 mg). Yield: 10%. m.p. 174°-175° C.

EXAMPLE 6 dl-3α-Acetoxy-8α-bromo-8β-fluoro-2,3,6,7,8,8aα-hexahydro-5,7-dioxo-5H-oxazolo[3,2-c]pyrimidine (12)

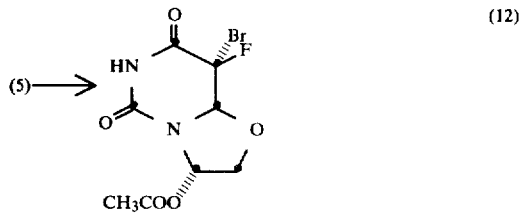

dl-8α-Bromo-8β-fluoro-3α-hydroxy-2,3,6,7,8,8aα-hexahydro-5,7-dioxo-5H-oxazolo[3,2-c]pyrimidine (5) (2.8 g, 10.4 mmol) is dissolved in acetic anhydride (200 ml), pyridine (10 ml) is added thereto, and then the mixture is allowed to stand at room temperature overnight. After removal of an excess amount of the reagent under reduced pressure, the product is purified by chromatography on a silica gel column employing a mixture of benzene-ethyl acetate (1:1) as eluent to give the title compound (12) (2.09 g). Yield: 65%. m.p. 128°-131° C. (Crystallized from benzene).

EXAMPLE 7 dl-8α-Bromo-8β-fluoro-2,3,6,7,8,8aα-hexahydro-3α-octanoyloxy-5,7-dioxo-5H-oxazolo[3,2-c]pyrimidine (13)

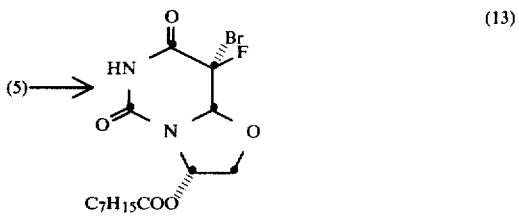

Octanoic anhydride (11.6 g, 42.8 mmol) and pyridine (1.73 ml, 21.4 mmol) are added to a solution of dl-8α-bromo-8β-fluoro-3α-hydroxy-2,3,6,7,8,8aα-hexahydro-5,7-dioxo-5H-oxazolo[3,2-c]pyrimidine (5) (2.89 g, 10.7 mmol) in tetrahydrofuran (50 ml), and the mixture is allowed to stand at room temperature overnight. The product obtained after removal of an excess amount of reagents and the solvent by distillation is purified by chromatography over silica gel employing a mixture of benzene-ethyl acetate (4:1) as eluent to give the titled compound (13) (2.94 g). Yield: 69.5%. Oily substance.

EXAMPLE 8 dl-8α-Bromo-8β-fluoro-2,3,6,7,8,8aα-hexahydro-5,7-dioxo-3α-trimethylacetoxy-5H-oxazolo[3,2-c]pyrimidine (14)

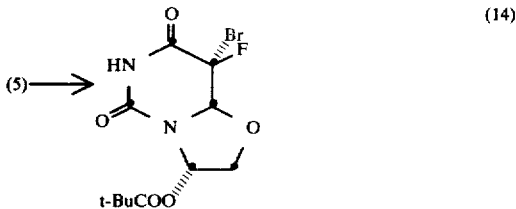

(A) dl-8α-Bromo-8β-fluoro-3α-hydroxy-2,3,6,7,8,8aα-hexahydro-5,7-dioxo-5H-oxazolo[3,2-c]pyrimidine (5) (5.26 g, 19.6 mmol) and pivalic anhydride (31.8 ml, 157 mmol) are dissolved in a mixture of tetrahydrofuran (50 ml) and acetonitrile (50 ml), and then tin tetrachloride (2.29 ml, 19.6 mmol) is added under ice cooling in dropwise fashion. The mixture is allowed to stand at room temperature for an additional 2 hours, and then sodium hydrogencarbonate (8.23 g, 98 mmol) and a small amount of water are added and stirred well at room temperature for 30 minutes. The insoluble material is filtered off, and the filtrate is evaporated to dryness under reduced pressure. The oily residue is purified by chromatography over silica gel employing a mixture of benzene-ethyl acetate (4:1) as eluent to give the title compound (14) (2.79 g). Yield: 40.3%. m.p. 188°–189° C. (Recrystallized from ether-petroleum ether).

(B) dl-8α-Bromo-8β-fluoro-3α-hydroxy-2,3,6,7,8,8aα-hexahydro-5,7-dioxo-5H-oxazolo[3,2-c]pyrimidine (5) (5.25 g, 19.5 mmol), pivalic anhydride (34.2 g, 183 mmol) and pyridine (1.89 ml, 23.4 mmol) are dissolved in tetrahydrofuran (150 ml), and dimethylaminopyridine (1.19 g, 9.8 mmol) is added, and the mixture is allowed to stand at 65° C. for 1.5 hours. After removal of an excess amount of reagents and the solvent under reduced pressure, the product is extracted with a mixture of ethyl acetate-acetonitrile. The organic layer is washed with an aqueous sodium hydrogencarbonate and saturated brine, dried on magnesium sulfate, and evaporated. The product is purified by chromatography over silica gel employing a mixture of benzene-ethyl acetate (4:1) as eluent to give the title compound (14) (2.45 g). Yield: 36%.

EXAMPLE 9 dl-3α-(tert-Butyldimethylsilyloxy)-8α-bromo-8β-fluoro-2,3,6,7,8,8aα-hexahydro-5,7-dioxo-5H-oxazolo[3,2-c]pyrimidine (15)

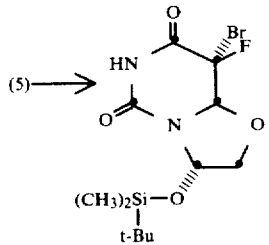

To a solution of tert-butyldimethylsilylimidazolide prepared by adding imidazole (2.39 g, 35.1 mmol) to a solution of tert-butyldimethylsilyl chloride (5.29 g, 35.1 mmol) in dimethylformamide (30 ml) is added a solution of dl-8α-bromo-8β-fluoro-3α-hydroxy-2,3,6,7,8,8aα-hexahydro-5,7-dioxo-5H-oxazolo[3,2-c]pyrimidine (5) (8.57 g, 31.9 mmol) in dimethylformamide (10 ml), and the mixture is allowed to stand at room temperature for 17 hours. The product is extracted with ethyl acetate. The ethyl acetate layer is washed with saturated brine, dried on magnesium sulfate, and evaporated. The product is purified by chromatography over silica gel employing a mixture of ethyl acetate-benzene (1:2) as eluent to give the title compound (15) (4.77 g). Yield: 39%. m.p. 152°–153° C.

EXAMPLE 10

Catalytic hydrogenation of dl-3α-(tert-butyldimethylsilyloxy)-8α-bromo-8β-fluoro-2,3,6,7,8,8aα-hexahydro-5,7-dioxo-5H-oxazolo[3,2-c]pyrimidine (15)-dl-3α-(tert-butyldimethylsilyloxy)-8α-fluoro-2,3,6,7,8,8aα-hexahydro-5,7-dioxo-5H-oxazolo[3,2-c]pyrimidine (16), dl-3α-(tert-butyldimethylsilyloxy)-8β-fluoro-2,3,6,7,8,8aα-hexahydro-5,7-dioxo-5H-oxazolo[3,2-c]pyrimidine (17) and dl-5-fluoro-1-(2-hydroxy-1-tert-butyldimethylsilyloxyethyl)-1,2,3,4-tetrahydro-2,4-dioxopyrimidine (18):

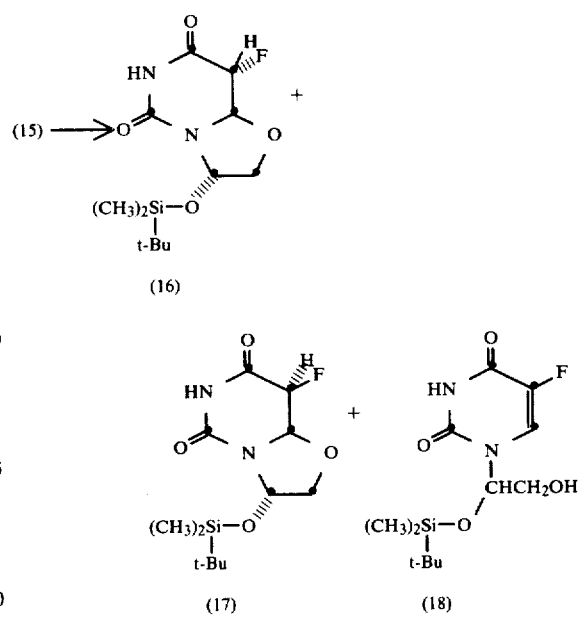

To a solution of dl-3α-(tert-butyldimethylsilyloxy)-8α-bromo-8β-fluoro-2,3,6,7,8,8aα-hexahydro-5,7-dioxo-5H-oxazolo[3,2-c]pyrimidine (15) (4.71 g, 12.3 mmol) in tetrahydrofuran (50 ml) are added sodium acetate (1.11 g, 13.5 mmol) and 10% palladium-carbon (470 mg), and the resulting suspension is hydrogenated under vigorous stirring in a hydrogen atmosphere. After about 4 hours a theoretical amount (275 ml) of hydrogen gas is absorbed; the insoluble material is filtered off, and then the solvent is distilled off. The product is separated by chromatography on a silica gel column employing a mixture of benzene-ethyl acetate (4:1) as eluent to give the compound (17) (245 mg) as the first fraction. Yield: 8.1%. m.p. 132°–133° C. (Recrystallized from methylene chloride-petroleum ether). The compound (16) (1.98 g) is obtained as the main product from the next fraction. Yield: 52.8%. m.p. 165°–166° C. (Recrystallized from methylene chloride-petroleum ether). The compound (18) (874 mg) is obtained from the polar fraction. Yield: 23.4%. m.p. 176°–179° C. (Recrystallized from methylene chloride-petroleum ether).

EXAMPLE 11 dl-8α-Fluoro-3α-hydroxy-2,3,6,7,8,8aα-hexahydro-5,7-dioxo-5H-oxazolo[3,2-c]pyrimidine (19)

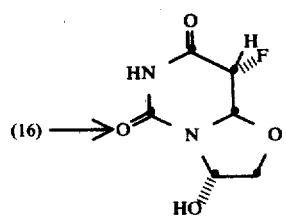

To a solution of dl-3α-(tert-butyldimethylsilyloxy)-8α-fluoro-2,3,6,7,8,8aα-hexahydro-5,7-dioxo-5H-oxazolo[3,2-c]pyrimidine (16) (1.585 g, 5.2 mmol) in acetonitrile (6.6 ml) is added 46% hydrofluoric acid aqueous solution (229 μl), and the mixture is allowed to stand at room temperature for 2 hours. The solvent is evaporated to dryness under reduced pressure, and the product is purified by chromatography over silica gel employing a mixture of benzene-ethyl acetate (1:1) as eluent and recrystallized from acetone-ether to give the title compound (19) (753 mg). Yield: 76%. m.p. 153°–158° C.

EXAMPLE 12 dl-3α-Acetoxy-8α-fluoro-2,3,6,7,8,8aα-hexahydro-5,7-dioxo-5H-oxazolo[3,2-c]pyrimidine (20) and dl-5-fluoro-1-(2-hydroxy-1-acetoxyethyl)-1,2,3,4-tetrahydro-2,4-dioxo-pyrimidine (21)

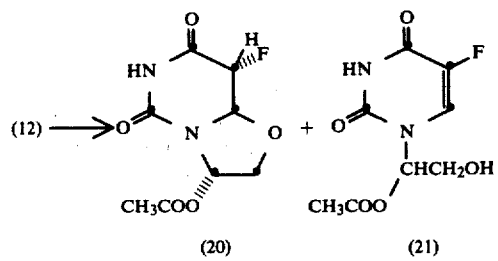

Anhydrous sodium acetate (946 mg, 11.5 mmol) and 10% palladium-carbon (300 mg) are suspended in a solution of dl-3α-acetoxy-8α-bromo-8β-fluoro-5,7-dioxo-2,3,6,7,8,8aα-hexahydro-5H-oxazolo[3,2-c]pyrimidine (12) (2.99 g, 9.6 mmol) dissolved in tetrahydrofuran (30 ml), and the mixture is catalytically hydrogenated under vigorous stirring in a hydrogen atmosphere. After about 3 hours a theoretical amount (215 ml) of hydrogen gas is absorbed; the insoluble material is filtered off, washed with acetonitrile thoroughly, and then the filtrate is evaporated to dryness. The resulting crystalline residue is recrystallized from acetone-methylene chloride to give the title compound (20) (1.08 g). The mother liquor is separated by chromatography on a silica gel column employing a mixture of benzene-ethyl acetate (1:1–1:2) as eluent to give the title compound (20) (0.49 g) as an additional crop (Total yield of the compound (20): 1.57 g; Yield: 69%). m.p. 182°–185° C. Additionally the compound (21) (0.17 g) is obtained from the polar fraction. Yield: 7.6%. m.p. 280°–285° C. (Recrystallized from acetone).

EXAMPLE 13 dl-8α-Fluoro-2,3,6,7,8,8aα-hexahydro-3α-octanoyloxy-5,7-dioxo-5H-oxazolo[3,2-c]pyrimidine (22) and dl-5-fluoro-1-(2-hydroxy-1-octanoyloxyethyl)-1,2,3,4-tetrahydro-2,4-dioxopyrimidine (23)

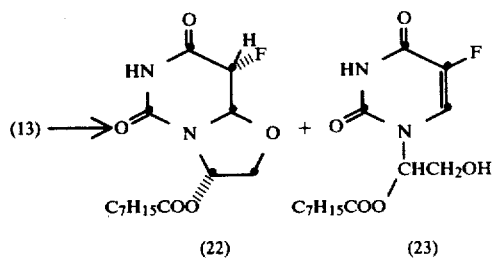

Anhydrous sodium acetate (1.22 g, 14.9 mmol) and 10% palladium-carbon (400 mg) are suspended in a solution of dl-8α-bromo-8β-fluoro-2,3,6,7,8,8aα-hexahydro-3α-octanoyloxy-5,7-dioxo-5H-oxazolo[3,2-c]pyrimidine (13) (2.94 g, 7.4 mmol) dissolved in tetrahydrofuran (70 ml), and the mixture is catalytically hydrogenated under vigorous stirring in a hydrogen atmosphere. After about 4 hours a theoretical amount (167 ml) of hydrogen gas is absorbed; the insoluble material is filtered off, washed with acetonitrile thoroughly, and then the filtrate is evaporated. The resulting crystalline residue is recrystallized from ether-petroleum ether to give the title compound (22) (0.9 g) as crystals of the first crop. Moreover, the mother liquor is separated by chromatography over silica gel employing a mixture of benzene-ethyl acetate (4:1–1:1) as eluent to give the title compound (22) (0.6 g) as crystals of the second crop. Total yield of the compound (22): 1.50 g. Yield: 63.7%. m.p. 138°–141° C. Additionally, the compound (23) (0.16 g) is obtained from the polar fraction. Yield: 6.8%. m.p. 107°–111° C. (Recrystallized from acetone-ether).

EXAMPLE 14

Catalytic hydrogenation of dl-8α-bromo-8β-fluoro-2,3,6,7,8,8aα-hexahydro-5,7-dioxo-3α-trimethylacetoxy-5H-oxazolo[3,2-c]pyrimidine (14)-dl-8α-fluoro-2,3,6,7,8,8aα-hexahydro-5,7-dioxo-3α-trimethylacetoxy-5H-oxazolo[3,2-c]pyrimidine (24), dl-8β-fluoro-2,3,6,7,8,8aα-hexahydro-5,7-dioxo-3α-trimethylacetoxy-5H-oxazolo[3,2-c]pyrimidine (11) and dl-5-fluoro-(2-hydroxy-1-trimethylacetoxyethyl)-1,2,3,4-tetrahydro-2,4-dioxopyrimidine (25)

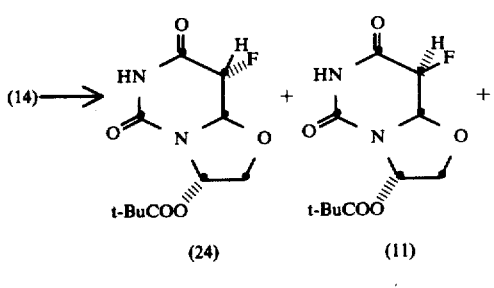

-continued

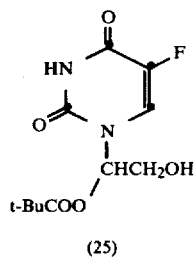

(25)

Anhydrous sodium acetate (1.39 g, 17 mmol) and 10% palladium-carbon (0.5 g) are suspended in a solution of the title compound (14) (5.0 g, 14.2 mmol) dissolved in tetrahydrofuran (50 ml), and the mixture is catalytically hydrogenated under vigorous stirring in a hydrogen atmosphere. After about 3 hours a theoretical amount (320 ml) of hydrogen gas is absorbed; the insoluble material is filtered off, and then the filtrate is evaporated. The resulting crystalline residue is recrystallized from acetone-ether to give the compound (24) (2.02 g). Yield: 52.0%. The mother liquor is separated by chromatography over silica gel employing a mixture of benzene-ethyl acetate (4:1–1:1) as eluent to give the compound (11) (372 mg) as the first fraction. Yield: 9.6%. m.p. 176°–177° C. (Recrystallized from acetone-ether). The compound (24) (480 mg) is obtained as the main product from the next fraction. Total amount of the compound (24): 2.50 g. Total yield: 64.4%. m.p. 164°–166° C. (Recrystallized from acetone-ether). Additionally, the compound (25) (20 mg) is obtained from the polar fraction. Yield: 0.5%. m.p. 151°–152° C. (Recrystallized from acetone-ether).

EXAMPLE 15

(A)

dl-5α-Bromo-6β-(3-butenyloxy)-5β-fluoro-1,2,3,4,5,6-hexahydro-2,4-dioxopyrimidine (26)

(i)

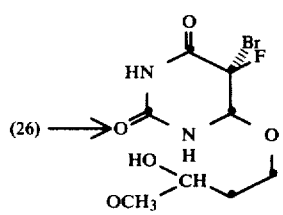

(26)

dl-5α-Bromo-5β-fluoro-1,2,3,4,5,6-hexahydro-6β-methoxy-2,4-dioxopyrimidine (1) (50 g, 207 mmol), 3-buten-1-ol (27 ml, 310 mmol) and methanesulfonic acid (5 ml) are dissolved in acetonitrile (500 ml), placed in a flask equipped with a Dien-Stark water separator charged with Molecular sieves 4A (60 g), and then refluxed with heating for 4 hours. After cooling, the product is extracted with ether. The ether layer is washed with an aqueous sodium hydrogen-carbonate and saturated brine, dried on magnesium sulfate, and the solvent is distilled off. The resulting crystals are washed with water several times and then dried to give the title compound (26) (36 g). Yield: 72%.

(3)→(26)    (ii)

To a solution of dl-6β-acetoxy-5α-bromo-5β-fluoro-1,2,3,4,5,6-hexahydro-2,4-dioxopyrimidine (3) (30 g, 110 mmol) and 3-buten-1-ol (14.6 ml, 165 mmol) dissolved in acetonitrile (500 ml) is added methanesulfonic acid (1 ml), and the mixture is allowed to stand at 70°–80° C. for 3 hours. The solvent and an excess amount of the reagent are evaporated, and water is added to the residue to give crystalline product. The product is collected by filtration, washed with water several times and dried to give the title compound (26) (21.5 g). Yield: 70%. m.p. 136.5°–139° C. (Recrystallized from ether-petroleum ether).

(B)

dl-5α-Bromo-5β-fluoro-6β-(3-hydroxy-3-methoxypropoxy)-1,2,3,4,5,6-hexahydro-2,4-dioxopyrimidine (27)

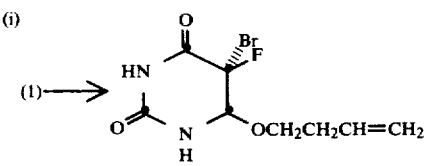

dl-5α-Bromo-6β-(3-butenyloxy)-5β-fluoro-1,2,3,4,5,6-hexahydro-2,4-dioxopyrimidine (26) (21.5 g, 77 mmol) is dissolved in a mixture solution of dichloromethane (400 ml) and methanol (200 ml), cooled to −70° C. in a dry ice-acetone bath and ozonized by introducing ozone gas. When the reaction mixture turns blue, supply of ozone is stopped, and an excess amount of ozone is exhausted by introducing nitrogen gas; then dimethylsulfide (41 ml) is added thereto, and the mixture is allowed to stand at 0° C. for 15 hours. The product obtained by removal of the solvents is purified by chromatography on a silica gel column employing a mixture of benzene-ethyl acetate (1:1–1:2) as eluent to give the title compound (27) (15.4 g). Yield: 63%. m.p. 99°–102° C.

(C)

dl-9α-Bromo-9β-fluoro-3,4,7,8,9,9aα-hexahydro-4α-hydroxy-6,8-dioxo-2H,6H-[1,3]-oxazino-[3,2-c]pyrimidine (28)

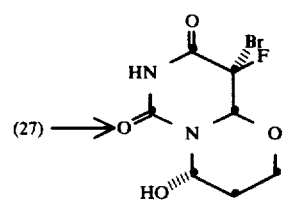

dl-5α-Bromo-5β-fluoro-6β-(3-hydroxy-3-methoxypropoxy)-1,2,3,4,5,6-hexahydro-2,4-dioxopyrimidine (27) (5.0 g, 15.9 mmol) is dissolved in acetone (30 ml) and water (30 ml), and 60% perchloric acid aqueous solution (5 ml) is added thereto; the mixture is allowed to stand at room temperature for 3 hours. After the reaction mixture is neutralized with sodium carbonate, the solvent is distilled off under reduced pressure. The remaining moisture is removed by azeotropic distillation with benzene as much as possible. Ether is added to the residue to extract the product, and sodium perchlorate which is insoluble in ether is removed by filtration. After removal of the solvent, the ether extract is purified by chromatography on a silica gel column employing a mixture of benzene-ethyl acetate (1:1) as eluent to give the title compound (28) (2.93 g). Yield: 65%. m.p. 137.5°–139.5° C. (Recrystallized from ether).

The mother liquor (about 9.3 g) after crystallization of dl-5α-bromo-5β-fluoro-6β-(3-hydroxy-3-methoxypropoxy)-1,2,3,4,5,6-hexahydro-2,4-dioxopyrimidine (27) obtained by the above mentioned ozonization reaction is dissolved in acetone (50 ml) and water (50 ml), and allowed to react with 60% aqueous perchloric acid (8.3 ml) at room temperature for 4 hours. The reaction mixture is worked up in the same manner as mentioned above to give the title compound (28) (4.19 g). Overall yield of the title compound (28) produced from dl-5α-bromo-6β-(3-butenyloxy)-5β-fluoro-1,2,3,4,5,6-hexahydro-2,4-dioxopyrimidine (26) (21.5 g) is 13.2 g. Yield: 60.6%.

EXAMPLE 16

(A)

dl-5β-Fluoro-6β-(3-butenyloxy)-1,2,3,4,5,6-hexahydro-2,4-dioxopyrimidine (29)

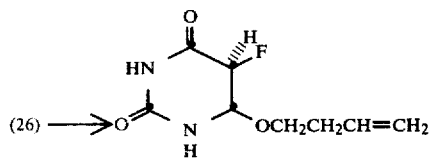

A solution of 86% potassium hydroxide (5.05 g, 77.4 mmol) dissolved in methanol (180 ml) is cooled to −5° C., and hydrogen sulfide (3.34 g, 98.3 mmol) is absorbed therein. dl-5α-Bromo-6β-(3-butenyloxy)-5β-fluoro-1,2,3,4,5,6-hexahydro-2,4-dioxopyrimidine (26) (22.9 g, 81.5 mmol) is added thereto and allowed to react at −5° C. for 10 minutes, at room temperature for 30 minutes, and then at 60° C. for 10 minutes, successively. After cooling, the reaction mixture is neutralized with sodium hydrogencarbonate, and the insoluble material is filtered off and washed with acetone. The filtrate is evaporated, and the crystalline residue is crystallized from acetone-petroleum ether to give the title compound (29) (8.2 g). Yield: 53%. m.p. 167°–169° C.

(B)

dl-5β-Fluoro-6β-(3-hydroxy-3-methoxypropoxy)-1,2,3,4,5,6-hexahydro-2,4-dioxopyrimidine (30)

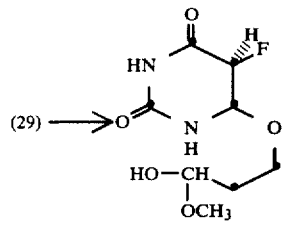

dl-5β-Fluoro-6β-(3-butenyloxy)-1,2,3,4,5,6-hexahydro-2,4-dioxopyrimidine (29) (10.2 g, 50.4 mmol) is dissolved in a mixture of dichloromethane (200 ml) and methanol (100 ml), cooled to −70° C. in a dry ice-acetone bath, and ozonized by introducing ozone gas. When the reaction mixture turns blue, supply of ozone is stopped, and an excess amount of ozone is exhausted by introducing nitrogen gas. Dimethyl sulfide (32 ml) is added thereto, and the mixture is allowed to stand at 0° C. for 1 hour. The solvent is removed by distillation, and the residue is dissolved in a mixture of benzene-ethyl acetate (1:2), passed through a silica gel column to remove dimethylsulfoxide and then evaporated to give the title compound (30) (7.78 g) as an oily crude product. The obtained product containing a small amount of the compound (30) is subjected to the following reaction.

(C)

dl-9β-Fluoro-4α-hydroxy-3,4,7,8,9,9aα-hexahydro-6,8-dioxo-2H,6H-[1,3]-oxazino[3,2-c]pyrimidine (31)

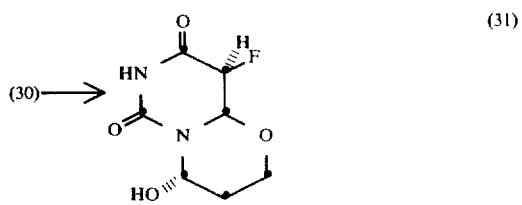

The crude dl-5β-fluoro-6β-(3-hydroxy-3-methoxypropoxy)-1,2,3,4,5,6-hexahydro-2,4-dioxopyrimidine (30) obtained in (B) is dissolved in a mixture of acetone (50 ml) and water (50 ml), to which conc. sulfuric acid (1 ml) is added, and allowed to stand at room temperature for 1 hour. The reaction mixture is neutralized with sodium carbonate, and the solvent is distilled off under reduced pressure. The residue is extracted with acetone to remove sodium sulfate produced, and the acetone extract is passed through a short column of silica gel. The eluate with acetone is evaporated, and the residue is recrystallized from acetone-ether to give the title compound (31) (3.73 g). Yield from the compound (29): 36%. m.p. 126°–128° C.

EXAMPLE 17 dl-4α-(tert-Butyldimethylsilyloxy)-7-tert-butyldimethylsilyl-9α-bromo-9β-fluoro-3,4,7,8,9,9aα-hexahydro-6,8-dioxo-2-H,6H-[1,3]-oxazino[3,2-c]pyrimidine (32)

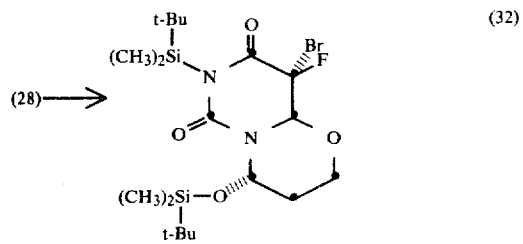

To a solution of tert-butyldimethylsilylimidazolide prepared by adding imidazole (5.61 g, 82.5 mmol) to a solution of tert-butyldimethylsilyl chloride (8.29 g, 55 mmol) in dimethylformamide (120 ml) is added dl-9α-bromo-9β-fluoro-3,4,7,8,9,9aα-hexahydro-4α-hydroxy-6,8-dioxo-2H,6H-[1,3]-oxazino[3,2-c]pyrimidine (28) (6.25 g, 22 mmol), and the mixture is allowed to stand at room temperature for 2.5 days. The product is extracted with ethyl acetate, and the ethyl acetate layer is washed with water, dried on magnesium sulfate, and evaporated. The residue is purified by chromatography on a silica gel column employing a mixture of benzene-ethyl acetate (9:1) as eluent to give the title compound (32) (6.06 g). Yield: 54%. m.p. 152°–155° C.

EXAMPLE 18

Catalytic hydrogenation of dl-4α-(tert-butyldimethylsilyloxy)-7-tert-butyldimethylsilyl-9α-bromo-9β-fluoro-3,4,7,8,9,9aα-hexahydro-6,8-dioxo-2H,6H-[1,3]-oxazino-[3,2-c]pyrimidine (32)

EXAMPLE 19 dl-9β-Fluoro-3,4,7,8,9,9aα-hexahydro-4α-hydroxy-6,8-dioxo-2H,6H-[1,3]-oxazino[3,2-c]pyrimidine (31), dl-9α-fluoro-3,4,7,8,9,9-aα-hexahydro-4α-hydroxy-6,8-dioxo-2H,6H-[1,3]-oxazino[3,2-c]pyrimidine (36) and dl-9α-fluoro-3,4,7,8,9,9-aα-hexahydro-4β-hydroxy-6,8-dioxo-2H,6H-[1,3]-oxazino[3,2-c]pyrimidine (37)

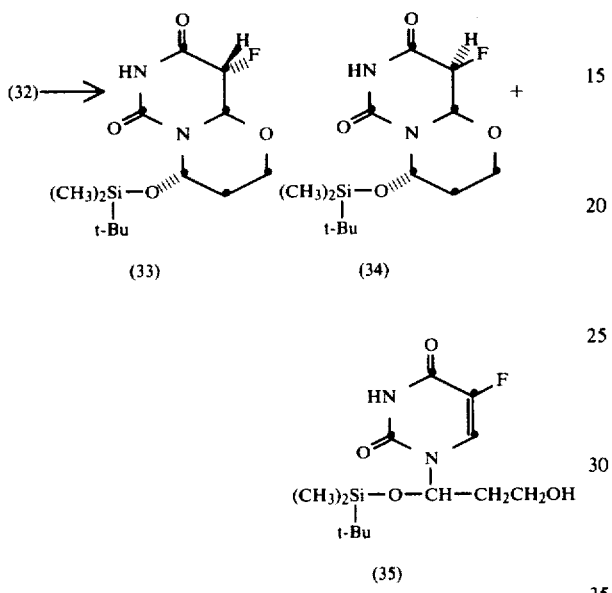

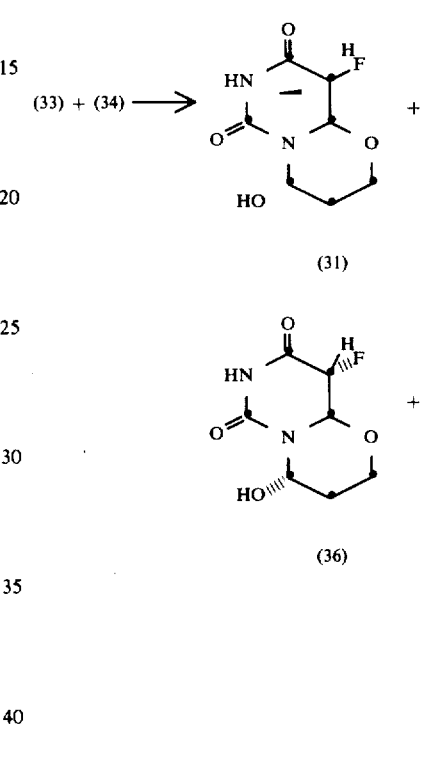

To a solution of the compound (32) 6.06 g, 11.9 mmol) dissolved in tetrahydrofuran (60 ml) are added 10% palladium-carbon (300 mg) and anhydrous sodium acetate (1.38 g, 16.8 mmol), and the mixture is hydrogenated under vigorous stirring in a hydrogen atmosphere. After about 4 hours a theoretical amount (533 ml) of hydrogen gas is absorbed; insoluble material is filtered off and washed with acetonitrile. The filtrate is evaporated, and the residue is separated by chromatography over silica gel employing a mixture of benzene-ethyl acetate (4:1–1:2) as eluent to give a mixture (3.06 g, Yield: 81%) of dl-4α-(tert-butyldimethylsilyloxy)-9α-fluoro-3,4,7,8,9,9aα-hexahydro-6,8-dioxo-2H,6H-[1,3]-oxazino[3,2-c]pyrimidine (33) and dl-4α-(tert-butyldimethylsilyloxy)-9β-fluoro-3,4,7,8,9,9aα-hexahydro-6,8-dioxo-2H,6H-[1,3]-oxazino[3,2-c]pyrimidine (34) (about 3:2), and from the polar fraction dl-5-fluoro-1-(3-hydroxy-1-tert-butyldimethylsilyloxypropyl)-1,2,3,4-tetrahydro-2,4-dioxopyrimidine (35) (331 mg, Yield: 8.7%). m.p. 131°–133° C.

To a solution of a mixture (2.64 g, 8.29 mmol) of dl-9α and 9β-fluoro-4α-(tert-butyldimethylsilyloxy)-3,4,7,8,9,9aα-hexahydro-6,8-dioxo-2H,6H-[1,3]-oxazino[3,2-c]-pyrimidine (33) and (34) dissolved in acetonitrile (12 ml) is added 4.6% aqueous hydrofluoric acid (381 μl) and the resultant mixture is allowed to stand at room temperature for 2 hours. The solvent is removed by distillation to give a residue, of which the acetone soluble part (1.61 g) is separated by chromatography on a silica gel column employing a mixture of benzene-ethyl acetate (1:2) as eluent to give at first the title compound (37) (m.p. 232°–234° C., recrystallized from acetone-ether) and subsequently the title compound (36) (m.p. 148°–152° C., recrystallized from acetone-ether) and finally the title compound (31) (m.p. 126°–128° C., recrystallized from acetone-ether).

EXAMPLE 20 dl-4α-Acetoxy-9α-bromo-9β-fluoro-3,4,7,8,9,9aα-hexahydro-6,8-dioxo-2H,6H-[1,3]-oxazino[3,2-c]pyrimidine (38)

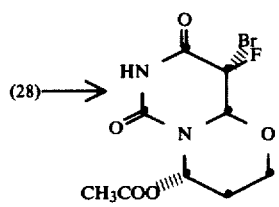

dl-9α-Bromo-9β-fluoro-3,4,7,8,9,9aα-hexahydro-4α-hydroxy-6,8-dioxo-2H,6H-[1,3]-oxazino[3,2-c]pyrimidine (28) (14.4 g, 50.9 mmol) is added to acetic anhydride (210 ml) and pyridine (4.1 ml, 50.9 mmol), and allowed to stand at room temperature for 15 hours. An excess amount of the reagents is distilled off, and the residue is purified by chromatography on a silica gel column employing a mixture of benzene-ethyl acetate (3:1) as eluent to give the title compound (38) (10.59 g). Yield: 64%. m.p. 171°–174° C. (Recrystallized from benzene).

EXAMPLE 21 dl-4α-Acetoxy-9α-fluoro-3,4,7,8,9,9aα-hexahydro-6,8-dioxo-2H,6H-[1,3]-oxazino[3,2-c]pyrimidine (39) and dl-4α-acetoxy-9β-fluoro-3,4,7,8,9,9aα-hexahydro-6,8-dioxo-2H,6H-[1,3]-oxazino[3,2-c]pyrimidine (40):

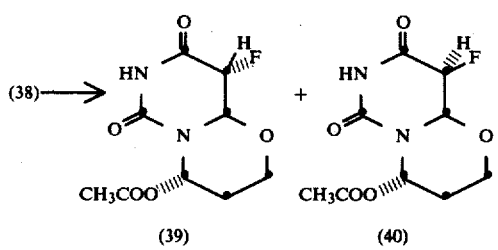

Anhydrous sodium acetate (2.57 g, 31.3 mmol) and 10% palladium-carbon (500 mg) are added to a solution of dl-4α-acetoxy-9α-bromo-9β-fluoro-3,4,7,8,9,9aα-hexahydro-6,8-dioxo-2H,6H-[1,3]-oxazino[3,2-c]pyrimidine (38) (8.48 g, 26.1 mmol) dissolved in tetrahydrofuran (100 ml), and the mixture is catalytically hydrogenated under vigorous stirring in a hydrogen atmosphere. After about 4 hours a theoretical amount (585 ml) of hydrogen gas is absorbed; the insoluble material is filtered off and then washed with acetonitrile. The filtrate is evaporated, and the residue is separated by chromatography on a silica gel column employing a mixture of benzene-ethyl acetate (1:1) as eluent to give dl-4α-acetoxy-9α-fluoro-3,4,7,8,9,9aα-hexahydro-6,8-dioxo-2H,6H-[1,3]-oxazino[3,2-c]pyrimidine (39) (2.55 g, Yield: 39.7%. m.p. 150°–154° C.) and dl-4α-acetoxy-9β-fluoro-3,4,7,8,9,9aα-hexahydro-6,8-dioxo-2H,6H-[1,3]-oxazino[3,2-c]pyrimidine (40) (1.37 g, Yield: 21.3%. m.p. 153.5°–155.5° C.).

EXAMPLE 22 dl-9α-Bromo-9β-fluoro-3,4,7,8,9,9aα-hexahydro-4α-octanoyloxy-6,8-dioxo-2H,6H-[1,3]-oxazino[3,2-c]pyrimidine (41)

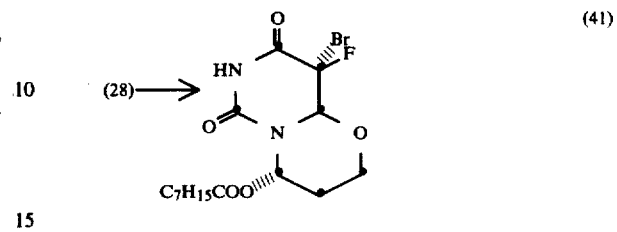

Dimethylaminopyridine (499 mg, 4 mmol) is added to a solution of dl-9α-bromo-9β-fluoro-3,4,7,8,9,9aα-hexahydro-4α-hydroxy-6,8-dioxo-2H,6H-[1,3]-oxazino[3,2-c]pyrimidine (28) (2.31 g, 8.1 mmol), octanoic anhydride (8.83 g, 32.4 mmol) and pyridine (0.66 ml, 8.1 mmol) dissolved in tetrahydrofuran (40 ml), and the mixture is allowed to stand at room temperature for 15 hours. The solvent is evaporated, and the residue is separated and purified by chromatography on a silica gel column employing a mixture of benzene-ethyl acetate (4:1) as eluent, and recrystallized from ether-petroleum ether to give the title compound (41) (1.29 g). Yield: 38.9%. m.p. 108°–110° C.

EXAMPLE 23 dl-9α-Bromo-9β-fluoro-3,4,7,8,9,9aα-hexahydro-6,8-dioxo-4α-trimethylacetoxy-2H,6H-[1,3]-oxazino[3,2-c]pyrimidine (42)

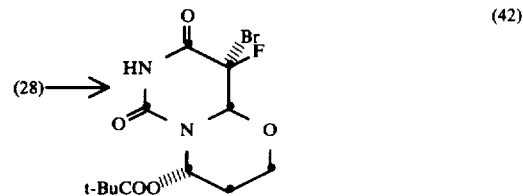

(i) dl-9α-Bromo-9β-fluoro-3,4,7,8,9,9aα-hexahydro-4α-hydroxy-6,8-dioxo-2H,6H-[1,3]-oxazino[3,2-c]pyrimidine (28) (820 mg, 2.9 mmol) and pivalic anhydride (4.7 ml, 23.2 mmol) are dissolved in a mixture of tetrahydrofuran (2 ml) and acetonitrile (8 ml), and tin tetrachloride (0.33 ml, 2.9 mmol) is added in dropwise fashion under ice cooling. The mixture is stirred at room temperature for additional 2 hours, and sodium hydrogencarbonate (1.34 g, 16 mmol) and a small amount of water are added and stirred well at room temperature for 30 minutes. The insoluble material is filtered off, and the filtrate is evaporated to dryness under reduced pressure. The oily residue is purified by chromatography over silica gel employing a mixture of benzene-ethyl acetate (2:1) as eluent to give the title compound (42) (186 mg). Yield: 16%. m.p. 178°–179.5° C. (Recrystallized from tetrahydrofuran-acetone).

(ii) dl-9α-Bromo-9β-fluoro-3,4,7,8,9,9aα-hexahydro-4α-hydroxy-6,8-dioxo-2H,6H-[1,3]-oxazino[3,2-c]pyrimidine (28) (10 g, 35.3 mmol), pivalic anhydride (46 ml, 226 mmol) and pyridine (2.86 ml, 35.3 mmol) are dissolved in tetrahydrofuran (70 ml), and dimethylaminopyridine (2.16 g, 17.7 mmol) is added thereto and allowed to stand at room temperature for 4 hours. The precipitated insoluble material is filtered off, and the filtrate is concentrated. The product is crystallized from tetrahydrofuran-acetone to give the title compound (42) (4.84 g). Moreover, the mother liquor is separated and purified by chromatography on a silica gel column employing a mixture of benzene-acetone (2:1) to give the title compound (42) (0.95 g) as an additional crop. Total amount: 5.79 g. Yield: 44.7%. m.p. 178°–179.5° C. (Recrystallized from tetrahydrofuran-acetone).

EXAMPLE 24 dl-9α-Fluoro-3,4,7,8,9,9aα-hexahydro-6,8-dioxo-4α-trimethylacetoxy-2H,6H-[1,3]-oxazino[3,2-c]pyrimidine (43)

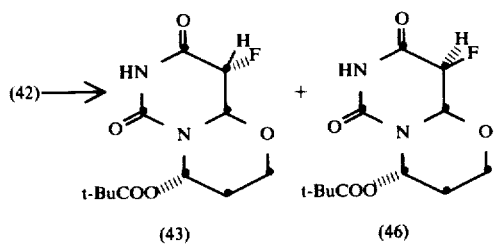

To a solution of dl-9α-bromo-9β-fluoro-3,4,7,8,9,9aα-hexahydro-6,8-dioxo-4α-trimethylacetoxy-2H,6H-[1,3]-oxazino[3,2-c]pyrimidine (42) (6.0 g, 16.3 mmol) in a mixture of methanol (50 ml) and tetrahydrofuran (240 ml) are added anhydrous sodium acetate (2 g, 24.5 mmol) and 10% palladium-carbon (600 mg), and the mixture is catalytically hydrogenated under vigorous stirring in a hydrogen atmosphere. After about 1 hour a theoretical amount (365 ml) of hydrogen gas is absorbed; the insoluble material is filtered off and washed with acetonitrile. The solvent is distilled off, and the residue is extracted with a mixture of ethyl acetate-acetonitrile. The organic layer is washed with an aqueous sodium hydrogencarbonate solution and saturated brine and dried on magnesium sulfate, and then evaporated to dryness. The residue is recrystallized from acetone-ether to give the title compound (43) (1.84 g). Yield: 39.2%. m.p. 163°–166° C. The mother liquor contains the title compound (43) and its 9β-fluoro-epimer i.e., dl-9β-fluoro-3,4,7,8,9,9aα-hexahydro-6,8-dioxo-4α-trimethylacetoxy-2H,6H-[1,3]oxazino[3,2-c]pyrimidine (46). The ratio of two isomers, 9α-fluoro to 9β-fluoro derivatives produced by catalytic hydrogenation is about 3:2, which is determined by NMR spectrum.

EXAMPLE 25 dl-9α-Fluoro-3,4,7,8,9,9aα-hexahydro-4α-octanoyloxy-6,8-dioxo-2H,6H-[1,3]-oxazino[3,2-c]pyrimidine (44)

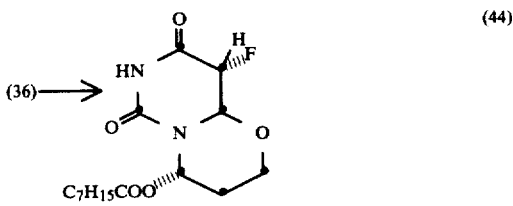

dl-9α-Fluoro-3,4,7,8,9,9aα-hexahydro-4α-hydroxy-6,8-dioxo-2H,6H-[1,3]-oxazino[3,2-c]pyrimidine (36) (408 mg, 2 mmol), octanoic anhydride (2.7 g, 10 mmol) and pyridine (1 ml, 12.7 mmol) are dissolved in tetrahydrofuran (5 ml) and allowed to stand at room temperature for 15 hours. An excess amount of reagents and the solvent are removed by distillaton under reduced pressure, and the product is purified by chromatography on a silica gel column employing a mixture of benzene-ethyl acetate (4:1) as eluent to give the title compound (44) (423 mg). Yield: 64%. m.p. 85°–86° C.

EXAMPLE 26 dl-9β-Fluoro-3,4,7,8,9,9aα-hexahydro-4α-octanoyloxy-6,8-dioxo-2H,6H-[1,3]-oxazino[3,2-c]pyrimidine (45)

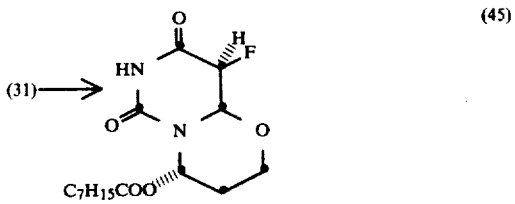

dl-9β-Fluoro-3,4,7,8,9,9aα-hexahydro-4α-hydroxy-6,8-dioxo-2H,6H-[1,3]-oxazino[3,2-c]pyrimidine (31) (100 mg, 0.49 mmol), octanoic anhydride (460 mg, 1.7 mmol) and pyridine (0.048 ml, 0.59 mmol) are dissolved in tetrahydrofuran (2 ml) and allowed to stand at room temperature for 15 hours. An excess amount of reagents and the solvent are removed by distillation under reduced pressure, and the product is purified by chromatography on a silica gel column employing a mixture of benzene-ethyl acetate (4:1) as eluent to give the title compound (45) (100 mg). Yield: 62%. Oily substance.

| Compound No. | Structural Formula | m.p., Molecular Formula | UV, IR Spectrum | NMR Spectrum (d$_6$-Acetone) |
|---|---|---|---|---|
| 2 | | mp 196–197° C.<br>C$_7$H$_8$BrFN$_2$O$_3$ (267.07)<br>Anal. C H N F<br>cal. 31.48 3.02 10.49 7.11<br>F   31.21 2.96 10.47 7.57 | IR(KBr) 3250<br>1754, 1717 cm$^{-1}$ | 4.27(2H,m), 5.5–5.1(3H,m), 6.3–5.6(1H,m), 8.08(1H,br), 9.87(1H, br) |

-continued

| Compound No. | Structural Formula | m.p., Molecular Formula | UV, IR Spectrum | NMR Spectrum (d$_6$-Acetone) |
|---|---|---|---|---|
| 4 | (structure with Br, F, HOCH-OCH$_3$ group) | mp 110–116° C.<br>C$_7$H$_{10}$BrFN$_2$O$_5$ (301.086)<br>Anal. C H N F<br>cal. 27.92 3.35 9.31 6.31<br>F  28.02 3.47 9.16 6.58 | IR(KBr) 3360, 3240, 1740, 1717 cm$^{-1}$ | 3.35(3H,S), 3.68(2H,d,J=5Hz), 4.68(1H,m), 5.35(1H,d,J=4.5Hz), 8.13(1H,br), 9.83(1H,br)<br>(+CO$_3$OD) 3.35(3H,S), 3.67(2H,d, J=5Hz), 4.67(1H,t,J=5Hz), 5.35 (1H,S) |
| 5 | (structure with Br, F, HO group) | mp 142–143° C.<br>C$_6$H$_6$BrFN$_2$O$_4$ (269.044)<br>Anal. C H N F<br>cal. 26.78 2.25 10.41 7.06<br>F  27.08 2.42 10.25 7.16 | IR(KBr) 3450, 3225, 1740, 1720 cm$^{-1}$ | 4.03(1H,dd,J=1&9Hz), 4.37(1H,dd, J=4&9Hz), 5.78(1H,d,J=18Hz), 5.97(1H,m) |
| 6 | (structure with F, allyl group) | mp 171–172° C.<br>C$_7$H$_9$FN$_2$O$_3$ (188.162)<br>Anal. C H N F<br>cal. 44.68 4.82 14.89 10.10<br>F  44.55 4.64 14.87 10.10 | IR(KBr) 3230, 1758, 1716 cm$^{-1}$ | 4.17(2H,m), 5.5–4.9(4H,m), 6.2–5.6(1H,m), 7.9(1H,br), 9.4(1H, br) |
| 7 | (structure with F, HO-CH-OCH$_3$ group) | mp 176–178° C.<br>C$_7$H$_{11}$FN$_2$O$_5$ (222.18)<br>Anal. C H N F<br>cal. 37.84 4.99 12.61 8.55<br>F  37.58 4.76 12.83 8.69 | IR(KBr) 3330, 1740, 1725 cm$^{-1}$ | 3.35(3H,S), 3.60(2H,d,J=5Hz), 4.67(1H,m), 4.93–5.33(2H,m), 5.47(1H,dd,J=4&36Hz), 7.8(1H, br), 11.0(1H,br)<br>(+D$_2$O) 3.37(3H,S), 3.61(2H,d, J=5Hz), 4.7(1H,t,J=5Hz), 5.10 (1H,dd,J=4&6Hz), 5.50(1H,dd,J= 4&40Hz) |
| 8 | (structure with F, HO group) | mp 188–191° C.<br>C$_6$H$_7$FN$_2$O$_4$ (190.136)<br>Anal. C H N F<br>cal. 37.90 3.71 14.74 9.99<br>F  37.84 3.73 14.77 9.98 | IR(KBr) 3395, 3246, 1738, 1677 cm$^{-1}$ | 3.93(1H,dd,J=2&9Hz), 4.28(1H, dd,J=4&9Hz), 4.98(1H,dd,J= 2&51Hz), 5.65(1H,dd,J=2&24Hz), 5.87(1H,m), 8.8–12(1H,br) |
| 9 | (structure with F, CH$_3$COO group) | mp 173–174° C.<br>C$_8$H$_9$FN$_2$O$_5$ (232.172)<br>Anal. C H N F<br>cal. 41.38 3.91 12.07 8.18<br>F  41.56 3.97 11.86 8.38 | IR(KBr) 3220, 1740, 1702 cm$^{-1}$ | 2.07(3H,S), 4.10(1H,dd,J=2&10 Hz), 4.40(1H,ddd,J=0.5,4&10Hz), 5.06(1H,dd,J=2&50Hz), 5.79(1H, dd,J=2&24Hz), 6.68(1H,dd,J= 2&4Hz), 10.0(1H,br) |
| 10 | (structure with F, C$_7$H$_{15}$COO group) | mp 58–61° C.<br>C$_{14}$H$_{21}$FN$_2$O$_5$ (316.33)<br>Anal. C H N F<br>cal. 53.15 6.69 8.86 6.01<br>F  53.21 6.70 8.86 6.04 | IR(KBr) 3270, 1740, 1723 cm$^{-1}$ | 0.87(3H,t,J=6Hz), 1.0–2.0(10H, m), 2.37(2H,t,J=6Hz), 4.12(1H, dd,J=2&10Hz), 4.42(1H,dd,J=4& 10Hz), 5.08(1H,dd,J=2&50Hz), 5.80(1H,dd,J=2&24Hz), 6.72(1H, dd,J=2&4Hz), 9.83(1H,br) |

-continued

| Compound No. | Structural Formula | m.p., Molecular Formula | UV, IR Spectrum | NMR Spectrum (d$_6$-Acetone) |
|---|---|---|---|---|
| 11 | (structure with (CH$_3$)$_3$CCOO-, F, H) | mp 176-177° C.<br>C$_{11}$H$_{15}$FN$_2$O$_5$ (274.25)<br>Anal. C H N F<br>cal. 48.17 5.51 10.22 6.93<br>F 48.06 5.39 10.26 7.06 | IR(KBr) 3290, 1723(br) | 1.20(9H,S), 4.08(1H,dd,J=2&10 Hz), 4.45(1H,dd,J=4&10Hz), 5.08(1H,dd,J=2&50Hz), 5.82(1H, dd,J=2&24Hz), 6.70(1H,dd,J=2& 4Hz) |
| 12 | (structure with CH$_3$COO-, Br, F) | mp 128-131° C.<br>C$_8$H$_8$BrFN$_2$O$_5$ (311.08)<br>Anal. C H N F<br>cal. 30.89 2.59 9.00 6.11<br>F 31.24 2.67 8.92 6.50 | IR(CHCl$_3$) 3370, 1745 cm$^{-1}$ | 2.10(3H,S), 4.20(1H,dd,J=1&10 Hz), 4.47(1H,ddd,J=0.5,4&10Hz), 5.75(1H,d,J=18Hz), 6.75(1H,dd, J=1&4Hz), 9.5-12.8(1H,br) |
| 13 | (structure with C$_7$H$_{15}$COO-, Br, F) | oil<br>C$_{14}$H$_{20}$BrFN$_2$O$_5$ (395.236) | IR(CHCl$_3$) 3370, 1740 cm$^{-1}$ | 0.90(3H,t,J=5Hz), 2.30(2H,t,J= 6Hz), 1.0-2.0(10H,m), 4.18(1H, dd,J=1&10Hz), 4.47(1H,ddd,J=0.5, 4&10Hz), 5.88(1H,d,J=19Hz), 6.77 (1H,dd,J=1&4Hz) |
| 14 | (structure with (CH$_3$)$_3$CCOO-, Br, F) | mp 188-189° C.<br>C$_{11}$H$_{14}$BrFN$_2$O$_5$ (353.156)<br>Anal. C H N F<br>cal. 37.41 4.00 7.93 5.38<br>F 37.35 3.81 7.87 5.58 | IR(CHCl$_3$) 3370, 1740 cm$^{-1}$ | 1.20(9H,S), 4.15(1H,dd,J=1&9 Hz), 4.47(1H,ddd,J=0.5,4&9Hz), 5.95(1H,d,J=18Hz), 6.77(1H,dd, J=1&4Hz) |
| 15 | (structure with SiO-, Br, F) | mp 152-153° C.<br>C$_{12}$H$_{20}$BrFN$_2$O$_4$Si (383.302)<br>Anal. C H N F<br>cal. 25.13 3.52 4.89 3.31<br>F 25.37 3.21 5.03 3.22 | IR(KBr) 1756, 1692 cm$^{-1}$ | (CD$_3$Cl) 0.13(3H,S), 0.22(3H,S), 0.92(9H,S), 4.03(1H,dd,J=1&8Hz), 4.28(1H,dd,J=4&8Hz), 5.60(1H,d, J=18Hz), 5.98(1H,dd,J=1&4Hz), 8.4(1H,br) |
| 16 | (structure with SiO-, F, H) | mp 165-166° C.<br>C$_{12}$H$_{21}$FN$_2$O$_4$Si (304.396)<br>Anal. C H N F<br>cal. 47.35 6.95 9.20 6.24<br>F 47.45 7.18 9.14 6.51 | IR(KBr) 1752, 1715(sh) 1688 cm$^{-1}$ | 0.16(3H,S), 0.22(3H,S), 0.90(9H, S), 3.90(1H,dd,J=1.5&9Hz), 4.32 (1H,dd,J=4.5&9Hz), 5.07(1H,dd, J=8.5&50.3Hz), 5.60(1H,dd,J= 8.5&10Hz), 5.87(1H,m) |

| Compound No. | Structural Formula | m.p., Molecular Formula | UV, IR Spectrum | NMR Spectrum (d$_6$-Acetone) |
|---|---|---|---|---|
| 17 | (structure with TMS-O group, fluorinated ring) | mp 132–133° C. C$_{12}$H$_{21}$FN$_2$O$_4$Si (304.396) Anal. C H N F cal. 47.35 6.95 9.20 6.24 F 47.52 7.18 9.13 6.23 | IR(KBr) 1736, 1698 cm$^{-1}$ | 0.13(3H,S), 0.23(3H,S), 0.92(9H, S), 3.95(1H,dd,J=8&1Hz), 4.25 (1H,dd,J=8&4Hz), 5.00(1H,dd,J= 50&2Hz), 5.70(1H,dd,J=24&2Hz), 5.98(1H,dd,J=1&4Hz), 9.67(1H, br) |
| 18 | (structure with TMS-O-CHCH$_2$OH group, 5-F uracil) | mp 176–179° C. C$_{12}$H$_{21}$FN$_2$O$_4$Si (304.396) Anal. C H N F cal. 47.35 6.95 9.20 6.24 F 47.19 7.04 9.02 6.51 | IV:λ$_{max}^{EtOH}$269mµ (ε=8,770) IR(KBr) 3400, 1710(br), 1660 cm$^{-1}$ | 0.10(3H,S), 0.17(3H,S), 0.92(9H, S), 3.73(2H,d,J=6Hz), 6.03(1H, dt,J=2&6Hz), 7.80(1H,d,J=7Hz) |
| 19 | (structure with HO group, fluorinated ring) | mp 153–158° C. C$_6$H$_7$FN$_2$O$_4$ (190.136) Anal. C H N F cal. 37.90 3.71 14.74 9.99 F 37.79 3.70 14.68 10.33 | IR(KBr) 3470, 1735, 1700 cm$^{-1}$ | 3.85(1H,dd,J=3&9.5Hz), 4.37(1H, dd,J=5&9.5Hz), 5.08(1H,dd,J= 8.5&49Hz), 5.58(1H,dd,J=8.5&11 Hz), 5.80(1H,m) |
| 20 | (structure with CH$_3$COO group, fluorinated ring) | mp 182–185° C. C$_8$H$_9$FN$_2$O$_5$ (232.172) Anal. C H N F cal. 41.39 3.91 12.07 8.18 F 41.12 4.12 11.07 8.15 | IR(Nujol) 1755 (sh), 1740, 1700 cm$^{-1}$ | 2.07(3H,S), 2.79(1H,br), 4.09 (1H,dd,J=2&10Hz), 4.47(1H,dd, J=4.5&10Hz), 5.30(1H,dd,J=8.5& 48.8Hz), 5.59(1H,dd,J=8.5&12 Hz), 6.58(1H,ddd,J=2.3&4.5Hz) |
| 21 | (structure with CH$_3$COO-CHCH$_2$OH group, 5-F uracil) | mp 280–285° C. C$_8$H$_9$FN$_2$O$_5$ (232.172) Anal. C H N F cal. 41.38 3.91 12.07 8.18 F 41.44 3.99 11.93 8.10 | VV:λ$_{max}^{EtOH}$266mµ (ε=8,300) IR(Nujol) 3500, 3200–3500, 1755, 1705, 1663 cm$^{-1}$ | 2.13(3H,S), 3.87(2H,d,J=5Hz), 6.77(1H,dt,J=2&5Hz), 7.85(1H,d, J=7Hz) |
| 22 | (structure with C$_7$H$_{15}$COO group, fluorinated ring) | mp 138–141° C. C$_{14}$H$_{21}$FN$_2$O$_5$ (316.33) Anal. C H N F cal. 53.15 6.69 8.86 6.01 F 52.51 6.51 8.82 5.96 | IR(CHCl$_3$) 3370, 1735 cm$^{-1}$ | 0.87(3H,t,J=5Hz), 1.0–2.0(10H, m), 2.35(3H,t,J=6Hz), 4.01(1H, dd,J=2&9Hz), 4.50(1H,dd,J=4&9 Hz), 5.18(1H,dd,J=8.5&50.4Hz), 5.68(1H,dd,J=8.5&9.6Hz), 6.58 (1H,m) |
| 23 | (structure with C$_7$H$_{15}$COO-CHCH$_2$OH group, 5-F uracil) | mp 107–111° C. C$_{14}$H$_{21}$FN$_2$O$_5$ (316.33) Anal. C H N F cal. 53.16 6.69 8.86 6.01 F 52.88 6.65 8.78 5.77 | VV:λ$_{max}^{EtOH}$266.5 mµ(ε=8,500) IR(CHCl$_3$) 3360, 3600–3300, 1757, 1710, 1670 cm$^{-1}$ | 0.88(3H,t,J=5Hz), 1.1–1.9(10H, m), 2.45(2H,t,J=7Hz), 3.93(2H, d,J=5Hz), 6.80(1H,dt,J=1&5Hz), 7.85(1H,d,J=7Hz) |

-continued

| Compound No. | Structural Formula | m.p., Molecular Formula | UV, IR Spectrum | NMR Spectrum (d$_6$-Acetone) |
|---|---|---|---|---|
| 24 | (structure with (CH$_3$)$_3$CCOO substituent) | mp 164–166° C.<br>C$_{11}$H$_{15}$FN$_2$O$_5$ (274.25)<br>Anal. C H N F<br>cal. 48.17 5.51 10.22 6.93<br>F 47.43 5.30 10.08 6.70 | IR(CHCl$_3$) 3380,<br>1740 cm$^{-1}$ | 1.20(9H,S), 4.00(1H,dd,J=2&10 Hz), 4.52(1H,dd,J=5&10), 5.18 (1H,dd,J=8&51.5Hz), 5.67(1H,dd, J=8&8.5Hz), 6.57(1H,m) |
| 25 | (structure with CHCH$_2$OH and (CH$_3$)$_3$CCOO) | mp 151–152° C.<br>C$_{11}$H$_{15}$FN$_2$O$_5$ (274.25)<br>Anal. C H N F<br>cal. 48.17 5.51 10.22 6.93<br>F 47.83 5.43 10.21 7.02 | UV: $\lambda_{max}^{MeOH}$ 266mμ<br>(ε=8,500)<br>IR(CHCl$_3$) 3380,<br>3550–3300, 1750,<br>1715 cm$^{-1}$ | 1.22(9H,S), 3.90(2H,d,J=5Hz), 6.73(1H,dt,J=2&5Hz), 7.82(1H, d,J=7Hz), |
| 26 | (structure with Br, F) | mp 136.5–139° C.<br>C$_8$H$_{10}$BrFN$_2$O$_3$ (281.096)<br>Anal. C H N F<br>cal. 34.18 3.59 9.97 6.76<br>F 33.86 3.49 9.88 6.91 | IR(Nujol) 1756,<br>1704 cm$^{-1}$ | 2.33(2H,m), 3.83(2H,m), 5.4–5.9(3H,m), 5.5–6.2(1H,m), 8.25 (1H,br) |
| 27 | (structure with Br, F, HO–CH–OCH$_3$) | mp 99–102° C.<br>C$_8$H$_{12}$BrFN$_2$O$_5$ (315.112)<br>Anal. C H N F<br>cal. 30.49 3.84 8.89 6.03<br>F 30.24 3.60 9.02 6.16 | IR(CHCl$_3$) 3380,<br>3100–3500, 1740 cm$^{-1}$ | 1.53–2.1(2H,m), 3.33(3H,S), 3.7–4.2(2H,m), 4.40(1H,t,J=6 Hz), 5.33(1H,dd,J=6&10Hz), 8.42 (1H,br), 9.92(1H br) |
| 28 | (structure with Br, F, HO) | mp 137.5–139.5° C.<br>C$_7$H$_8$BrFN$_2$O$_4$ (283.07)<br>Anal. C H N F<br>cal. 29.70 2.85 9.90 6.71<br>F 29.79 2.86 9.62 6.81 | IR(Nujol) 3400,<br>3100–3500, 1740,<br>1710 cm$^{-1}$ | 1.5–2.5(2H,m), 3.8–4.6(2H,m), 5.7(1H,S), 5.97(1H,m), 9.3–11.0(1H,br) |
| 29 | (structure with F) | mp 167–169° C.<br>C$_8$H$_{11}$FN$_2$O$_3$ (202.188)<br>Anal. C H N F<br>cal. 47.52 5.48 13.86 9.40<br>F 47.17 5.33 13.76 9.31 | IR(Nujol) 1750<br>1720, 1700 cm$^{-1}$ | 2.30(2H,m), 3.3–4.1(2H,m), 4.8–5.4(3H,m), 5.5–6.2(2H,m), 8.03 (1H,br), 9.87(1H,br) |
| 30 | (structure with F, HO–CH–OCH$_3$) | C$_8$H$_{13}$FN$_2$O$_5$ (236.206) | IR(Nujol) 3100–3500, 1742, 1715, 1685 cm$^{-1}$ | |

-continued

| Compound No. | Structural Formula | m.p., Molecular Formula | UV, IR Spectrum | NMR Spectrum (d$_6$-Acetone) |
|---|---|---|---|---|
| 31 | | mp 126–128° C.<br>C$_7$H$_9$FN$_2$O$_4$ (204.162)<br>Anal. C H N F<br>cal. 41.18 4.44 13.72 9.31<br>F 41.42 4.17 13.80 9.41 | IR(Nujol) 3480,<br>1740, 1690 cm$^{-1}$ | 1.5–2.4(2H,m), 3.7–4.5(2H,m),<br>5.27(1H,dd,J=4&36Hz), 5.70(1H,<br>dd,J=4&6Hz), 5.95(1H,m) |
| 32 | | mp 152–155° C.<br>C$_{19}$H$_{36}$BrFN$_2$O$_4$Si$_2$ (511.588)<br>Anal. C H N F<br>cal. 44.60 7.09 5.48 3.71<br>F 44.82 7.31 5.29 3.98 | IR(CHCl$_3$) 3380,<br>1760, 1710 cm$^{-1}$ | 0.03(6H,S), 0.22(6H,S), 0.90<br>(9H,S), 0.98(9H,S), 1.4–2.4<br>(2H,m), 3.8–4.6(2H,m), 5.67<br>(1H,S), 6.07(1H,m) |
| 33 | | mp 134–137° C.<br>C$_{13}$H$_{23}$FN$_2$O$_4$Si (318.422)<br>Anal. C H N F<br>cal. 49.03 7.28 8.80 5.97<br>F 49.02 7.53 8.71 6.31 | IR(CHCl$_3$) 3380,<br>1750, 1710 cm$^{-1}$ | 0.17(6H,S), 0.95(9H,S), 1.4–<br>2.0(2H,m), 3.7–4.7(2H,m), 5.18<br>(1H,dd,J=4&29Hz), 5.58(1H,dd,J<br>=4&12Hz), 5.92(1H,m) |
| 34 | | mp 122–125° C.<br>C$_{13}$H$_{23}$FN$_2$O$_4$Si (318.422)<br>Anal. C H N F<br>cal. 49.03 7.28 8.80 5.97<br>F 49.23 7.52 8.75 5.84 | IR(CHCl$_3$) 3380,<br>1755, 1710 cm$^{-1}$ | 0.10(3H,S), 0.17(3H,S), 0.90<br>(9H,S), 1.5–2.0(2H m), 3.8–<br>4.4(2H,m), 4.95(1H,dd,J=7&30<br>Hz), 5.45(1H,dd,J=7&9Hz), 5.95<br>(1H,m) |
| 35 | | mp 131–133° C.<br>C$_{13}$H$_{23}$FN$_2$O$_4$Si (318.422)<br>Anal. C H N F<br>cal. 49.03 7.28 8.80 5.97<br>F 49.15 7.47 8.65 5.78 | UV:$\lambda_{max}^{EtOH}$269mμ<br>($\epsilon$=8,700)<br>IR(CHCl$_3$) 3390,<br>1705, 1675 cm$^{-1}$ | 0.08(3H S), 0.20(3H,S), 0.92<br>(9H,S), 1.8–2.2(2H,m), 3.67<br>(2H,d,J=6Hz), 6.23(1H,dt,J=2&<br>6Hz), 7.77(1H,d,J=6Hz) |
| 36 | | mp 148–152° C.<br>C$_7$H$_9$FN$_2$O$_4$ (204.162)<br>Anal. C H N F<br>cal. 41.18 4.44 13.72 9.31<br>F 41.44 4.35 13.38 9.51 | IR(Nujol) 3100–<br>3500, 1760,<br>1732, 1715,<br>1690 cm$^{-1}$ | 1.6–2.1(2H,m), 3.8–4.4(2H,m),<br>4.97(1H,dd,J=8&30Hz), 5.45<br>(1H,dd,J=8&9Hz), 5.85(1H,m) |
| 37 | | mp 232–234° C.<br>C$_7$H$_9$FN$_2$O$_4$ (204.162)<br>Anal. C H N F<br>cal. 41.18 4.44 13.72 9.31<br>F 40.75 4.09 13.93 9.39 | IR(Nujol) 3100–<br>3500, 1765, 1750,<br>1715, 1682 cm$^{-1}$ | 1.7–2.2(2H,m), 3.8–4.2(2H,m),<br>4.97(1H,dd,J=8&30Hz), 5.47<br>(1H,dd,J=8&9Hz), 5.85(1H,m) |

-continued

| Compound No. | Structural Formula | m.p., Molecular Formula | UV, IR Spectrum | NMR Spectrum (d$_6$-Acetone) |
|---|---|---|---|---|
| 38 | (structure with Br, F, CH$_3$COO) | mp 171–174° C. C$_9$H$_{10}$BrFN$_2$O$_5$ (325.106) Anal. C H N F cal. 33.25 3.10 8.62 5.84 F 33.19 3.12 8.44 6.13 | IR(CHCl$_3$) 3380, 1760, 1710 cm$^{-1}$ | 1.83–2.57(2H,m), 2.17(1H,S), 4.1–5.6(2H,m), 5.70(1H,d,J=2Hz), 6.83(1H,m) |
| 39 | (structure with H, F, CH$_3$COO) | mp 150–154° C. C$_9$H$_{11}$FN$_2$O$_5$ (246.198) Anal. C H N F cal. 43.91 4.50 11.38 7.72 F 44.15 4.48 11.35 7.95 | IR(Nujol) 1760, 1730, 1710 cm$^{-1}$ | 2.03(3H,S), 1.7–2.3(2H,m), 3.9–4.3(2H,m), 5.03(1H,dd,J=8&24Hz), 5.53(1H,dd,J=8&12Hz), 6.77(1H,m) |
| 40 | (structure with H, F, CH$_3$COO) | mp 153.5–155.5° C. C$_9$H$_{11}$FN$_2$O$_5$ (246.198) Anal. C H N F cal. 43.91 4.50 11.38 7.72 F 44.19 4.14 11.43 7.90 | IR(Nujol) 1760, 1735 cm$^{-1}$ | 2.10(3H,S), 1.8–2.4(2H,m), 4.0–4.3(2H,m), 5.23(1H,dd,J=4&32Hz), 5.67(1H,dd,J=4&8Hz), 6.78(1H,m) |
| 41 | (structure with Br, F, C$_7$H$_{15}$COO) | mp 107–110° C. C$_{15}$H$_{22}$BrFN$_2$O$_5$ (409.262) Anal. C H N F cal. 44.02 5.42 6.85 4.64 F 44.14 5.45 6.70 4.58 | IR(CHCl$_3$) 3380, 1760, 1710 cm$^{-1}$ | 0.88(3H,t,J=5Hz), 1.1–2.4(2H and 10H,m), 2.50(2H,t,J=7Hz), 4.0–4.6(2H,m), 5.63(1H,d,J=2Hz), 6.83(1H,m) |
| 42 | (structure with Br, F, (CH$_3$)$_3$CCO-O) | mp 178–179.5° C. C$_{12}$H$_{16}$BrFN$_2$O$_5$ (367.182) Anal. C H N F cal. 39.25 4.39 7.63 5.17 F 39.77 4.41 7.35 4.95 | IR(Nujol) 1760, 1745, 1690 cm$^{-1}$ | 1.25(9H,S), 1.8–2.4(2H,m), 4.0–4.5(2H,m), 5.58(1H,d,J=2Hz), 6.80(1H,m) |
| 43 | (structure with H, F, (CH$_3$)$_3$CCO-O) | mp 163–166° C. C$_{12}$H$_{17}$FN$_2$O$_5$ (288.276) Anal. C H N F cal. 49.99 5.95 9.72 6.59 F 49.78 5.85 9.58 6.67 | IR(Nujol) 1760, 1730, 1700 cm$^{-1}$ | 1.20(9H,S), 1.7–2.6(2H,m), 3.9–4.3(2H,m), 5.08(1H,dd,J=8&34Hz), 5.58(1H,dd,J=8&8.5 Hz), 6.77(1H m) |
| 44 | (structure with H, F, C$_7$H$_{15}$COO) | mp 85–86° C. C$_{15}$H$_{23}$FN$_2$O$_5$ (330.356) Anal. C H N F cal. 54.53 6.99 8.48 5.75 F 54.45 6.94 8.45 5.78 | IR(CHCl$_3$) 1740, 3380 cm$^{-1}$ | 0.87(3H,t,J=5Hz), 1.1–2.4(2H& 10H,m), 2.37(2H,t,J=7Hz), 3.9–4.4(2H,m), 5.07(1H,dd,J=8&29.5 Hz), 5.55(1H,dd,J=8&12Hz), 6.85(1H,m) |

-continued

| Compound No. | Structural Formula | m.p., Molecular Formula | UV, IR Spectrum | NMR Spectrum (d$_6$-Acetone) |
|---|---|---|---|---|
| 45 | 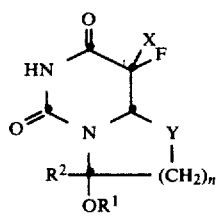 | oil<br>C$_{15}$H$_{23}$FN$_2$O$_5$ (330.356) | IR(CHCl$_3$) 3380,<br>1750, 1710 cm$^{-1}$ | 0.88(3H,t,J=5Hz), 1.1-2.4(2H&<br>10H,m), 2.42(2H,t,J=6Hz), 3.9<br>-4.3(2H,m), 5.17(1H,dd,J=4&<br>32Hz), 5.63(1H,dd,J=4&8Hz),<br>6.75(1H,m) |

What is claimed is:

1. A compound of the formula wherein
R$^1$ is hydrogen, C$_1$-C$_5$alkyl, C$_6$-C$_{10}$aryl, C$_7$-C$_{10}$aralkyl, C$_1$-C$_{12}$alkanoyl, C$_2$-C$_6$alkoxycarbonyl, C$_1$-C$_5$alkanoyloxymethyl, carbamoyl or tri-C$_1$-C$_5$alkylsilyl;

R$^2$ is hydrogen, C$_1$-C$_5$alkyl, C$_6$-C$_{10}$aryl or C$_7$-C$_{10}$aralkyl;

X is hydrogen, halogen or C$_2$-C$_6$alkoxycarbonyl;

Y is O, NR' (R' is hydrogen or C$_1$-C$_5$alkyl), S, SO or SO$_2$; and n is an integer of 1-3.

2. A compound claimed in claim 1, namely dl-8α-fluoro-2,3,6,7,8,8aα-hexahydro-5,7-dioxo-3α-trimethylacetoxy-5H-oxazolo[3,2-c]pyrimidine.

3. A compound claimed in claim 1, namely dl-8α-fluoro-2,3,6,7,8,8aα-hexahydro-3α-octanoyloxy-5,7-dioxo-5H-oxazolo[3,2-c]pyrimidine.

4. A compound claimed in claim 1, namely dl-3α-acetoxy-8α-fluoro-2,3,6,7,8,8aα-hexahydro-5,7-dioxo-5H-oxazolo[3,2-c]pyrimidine.

5. A compound claimed in claim 1, namely dl-9α-fluoro-3,4,7,8,9,9aα-hexahydro-6,8-dioxo-4α-trimethylacetoxy-2H,6H-[1,3]-oxazino[3,2-c]pyrimidine.

* * * * *